US011328790B2

(12) United States Patent
Braun et al.

(10) Patent No.: US 11,328,790 B2
(45) Date of Patent: May 10, 2022

(54) BIOMARKERS OF ENDOGENOUS BIOLOGICAL TIME

(71) Applicant: Northwestern University, Evanston, IL (US)

(72) Inventors: Rosemary Braun, Chicago, IL (US); Ravi Aliada, Glenview, IL (US); Phyllis Zee, Chicago, IL (US)

(73) Assignee: Northwestern University, Evanston, IL (US)

( * ) Notice: Subject to any disclaimer, the term of this patent is extended or adjusted under 35 U.S.C. 154(b) by 750 days.

(21) Appl. No.: 16/000,607

(22) Filed: Jun. 5, 2018

(65) Prior Publication Data

US 2018/0357360 A1 Dec. 13, 2018

Related U.S. Application Data

(60) Provisional application No. 62/515,361, filed on Jun. 5, 2017.

(51) Int. Cl.
*G16B 5/00* (2019.01)
*C12Q 1/6876* (2018.01)
*G16B 25/10* (2019.01)
*C12Q 1/6883* (2018.01)
*G16B 40/20* (2019.01)

(52) U.S. Cl.
CPC ............. *G16B 5/00* (2019.02); *C12Q 1/6876* (2013.01); *C12Q 1/6883* (2013.01); *G16B 25/10* (2019.02); *G16B 40/20* (2019.02); *C12Q 2600/158* (2013.01)

(58) Field of Classification Search
None
See application file for complete search history.

(56) References Cited

U.S. PATENT DOCUMENTS

2018/0071272 A1* 3/2018 Hogenesch .......... A61K 31/366

OTHER PUBLICATIONS

Ziemann et al. Gene name errors are widespread in the scientific literature. 2016. Genome Biology. vol. 17, No. 177, 3 pages. (Year: 2016).*
Braun et al. Universal method for robust detection of circadian state from gene expression. Sep. 10, 2018. PNAS. vol. 115, No. 39, E9247-E9256. (Year: 2018).*
Archer et al., (2008) Inter-individual differences in habitual sleep timing and entrained phase of endogenous circadian rhythms of BMAL1, PER2 and PER3 mRNA in human leukocytes. Sleep 31(5):608-17.
Archer et al., (2014) Mistimed sleep disrupts circadian regulation of the human transcriptome. Proceedings of the National Academy of Sciences 111(6):E682-E691.
Arnardottir et al., (2014) Blood-gene expression reveals reduced circadian rhythmicity in individuals resistant to sleep deprivation. Sleep 37(10):1589.
Barion et al., (2007) A clinical approach to circadian rhythm sleep disorders. Sleep Med 8(6):566-77.
Benloucif et al., (2005) Stability of melatonin and temperature as circadian phase markers and their relation to sleep times in humans. J Biol Rhythms 20(2):178-88.
Boivin et al., (2003) Circadian clock genes oscillate in human peripheral blood mononuclear cells. Blood 102(12):4143-5.
Chang et al., (2009) Sleep timing and circadian phase in delayed sleep phase syndrome. J Biol Rhythms 24(4):313-21.
Davis et al., (2007) GEOquery: a bridge between the Gene Expression Omnibus (GEO) and BioConductor. Bioinformatics 14:1846-1847.
Doherty et al., (2010) Circadian control of global gene expression patterns. Annu Rev Genet 44:419-44.
Eastman et al., (2005) Advancing circadian rhythms before eastward flight: a strategy to prevent or reduce jet lag. Sleep 28(1):33-44.
Friedman et al., (2010) A note on the group lasso and a sparse group lasso. arXiv:1001.0736. 8 pages.
Hughey et al., (2016) ZeitZeiger: supervised learning for high-dimensional data from an oscillatory system. Nucleic Acids Research 44(8):e80-e80.
Hughey, (2016) MetaPredict package vignette (github.com/jakejh/metapredict), v.0.0.0.9005 edition. 3 pages.
Hughey, (2016) ZeitZeiger package vignette (github.com/jakejh/zeitzeiger), v.0.0.0.9021 edition. 3 pages.
Hughey, (2017) Machine learning identifies a compact gene set for monitoring the circadian clock in human blood. Genome Medicine 9(1):19.
Johnson et al., (2007) Adjusting batch effects in microarray expression data using empirical bayes methods. Biostatistics 8(1):118-127.
Jones et al., (1999) Familial advanced sleep-phase syndrome: A short-period circadian rhythm variant in humans. Nat Med 5(9):1062-5.
Ko et al., (2006) Molecular components of the mammalian circadian clock. Hum Mol Genet 15 Spec No. 2:R271-7.
Laing et al., (2017) Blood transcriptome based biomarkers for human circadian phase. eLife 6:e20214.
Lemmer, (2006) Clinical chronopharmacology of the cardiovascular system: hypertension and coronary heart disease. Clin Ter 157(1):41-52.
Levi et al., (2007) Circadian rhythms: mechanisms and therapeutic implications. Annu Rev Pharmacol Toxicol 47:593-628.
Moller-Levet et al., (2013) Effects of insufficient sleep on circadian rhythmicity and expression amplitude of the human blood transcriptome. Proc Natl Acad Sci U S A 110(12):E1132-41.

(Continued)

*Primary Examiner* — Channing S Mahatan
(74) *Attorney, Agent, or Firm* — Casimir Jones SC; David W. Staple

(57) ABSTRACT

Provided herein are biomarkers of endogenous biological time (e.g. circadian time). In particular compositions and methods are provided for assessing the biological time of a subject, and diagnosis of diseases/conditions and/or providing treatments based thereon.

9 Claims, 7 Drawing Sheets

(56) References Cited

OTHER PUBLICATIONS

Patel et al., (2012) CircadiOmics: integrating circadian genomics, transcriptomics, proteomics and metabolomics. Nature methods 9(8):772-773.

Patel et al., (2015) The pervasiveness and plasticity of circadian oscillations: the coupled circadian-oscillators framework. Bioinformatics p. btv353.

Puttonen et al., (2010) Shift work and cardiovascular disease—pathways from circadian stress to morbidity. Scand J Work Environ Health 36(2):96-108.

R Core Team (2015) R: A Language and Environment for Statistical Computing (R Foundation for Statistical Computing, Vienna, Austria). Http://www.R-project.org/, retrieved Apr. 13, 2021, 12 pages.

Roenneberg et al., (2003) Life between clocks: daily temporal patterns of human chronotypes. J Biol Rhythms 18(1):80-90.

Roenneberg et al., (2007) Epidemiology of the human circadian clock. Sleep Med Rev 11(6):429-38.

Shields, (2002) Shift work and health. Health Reports 13(4):11-33.

Stratmann et al., (2006) Properties, entrainment, and physiological functions of mammalian peripheral oscillators. J Biol Rhythms 21(6):494-506.

Toh et al., (2001) An hper2 phosphorylation site mutation in familial advanced sleep phase syndrome. Science 291(5506):1040-3.

Ueda et al., (2004) Molecular-timetable methods for detection of body time and rhythm disorders from single-time-point genome-wide expression profiles. Proc Natl Acad Sci U S A 101(31):11227-32.

Videnovic et al., (2014) Circadian melatonin rhythm and excessive daytime sleepiness in parkinson disease. JAMA Neurol 71(4):463-9.

Wheeler et al., (2007) Database resources of the National Center for Biotechnology Information. Nucleic acids research 35(Database issue):D5.

Xu et al., (2005) Functional consequences of a CKIdelta mutation causing familial advanced sleep phase syndrome. Nature 434(7033):640-4.

Zhang et al., (2014) A circadian geneexpression atlas in mammals: implications for biology and medicine. Proceedings of the National Academy of Sciences 111(45):16219-16224.

Zou et al., (2005) Regularization and variable selection via the elastic net. Journal of the Royal Statistical Society Series B—Statistical Methodology 67:301-320.

\* cited by examiner

BIOMARKERS OF ENDOGENOUS BIOLOGICAL TIME

CROSS-REFERENCE TO RELATED APPLICATIONS

The present invention claims the priority benefit of U.S. Provisional Patent Application 62/515,361, filed Jun. 5, 2017, which is incorporated by reference in its entirety.

STATEMENT REGARDING FEDERALLY SPONSORED RESEARCH OR DEVELOPMENT

This invention was made with government support under HR0011515023 awarded by the Defense Advanced Research Projects Agency (DARPA). The government has certain rights in the invention.

FIELD

Provided herein are biomarkers of endogenous biological time (e.g. circadian time). In particular compositions and methods are provided for assessing the biological time of a subject, and diagnosis of diseases/conditions and/or providing treatments based thereon.

BACKGROUND

Human genomes are temporally organized by circadian clocks with respect to the 24 hour environment. Circadian clocks are not only found in discrete areas of the brain, but are found in virtually every organ in our bodies. Disruptions in circadian clocks, or chronopathology, may underlie various forms of neurological, cardiovascular, and metabolic disease.

SUMMARY

Provided herein are biomarkers of endogenous biological time (e.g. circadian time). In particular compositions and methods are provided for assessing the biological time of a subject, and diagnosis of diseases/conditions and/or providing treatments based thereon.

In some embodiments, provided herein are methods of determining the biological time-of-day of a subject, the method comprising: (a) detecting the level of one or more biomarkers of Table 1 in two samples obtained from the subject at timepoints spaced by at least 4 hours; (b) applying a predictor algorithm described herein to the levels of biomarkers detected in the two (or more (e.g., 3, 4, 5, 6, 7, 8) samples; and (c) determining the biological time-of-day for the subject based on output of the predictor algorithm. In some embodiments, the samples are a blood sample. In some embodiments, the levels of 4 or more (e.g., 4, 5, 6, 7, 8, 9, 10, 12, 14, 16, 18, 20, 25, 30, 35, 40, 41, or ranges therebetween) biomarkers of Table 1 are detected. In some embodiments, the levels of one or more (e.g., 2, 4, 6, 8, 10, 12, 14, 16, 18, or ranges therebetween) of CLEC10A, PER1, GHRL, IL1B, NR1D1, DDIT4, GNG2, LLGL2, NR1D2, CD1C, DHRS13, GPCPD1, TIAM2, CD38, GZMB, ZNF438, EPHX2, and PDK1 are detected. In some embodiments, the levels of each of the biomarkers of Table 1 are detected. In some embodiments, the biomarker levels are detected by microarray, RNA-Seq, or any suitable technique. In some embodiments, the predictor algorithm comprises a within-subject normalization procedure.

In some embodiments, provided herein are methods of detecting chronopathology in a subject comprising (a) determining the biological time-of-day of a subject using the methods herein; and (b) comparing the biological time-of-day of a subject to the actual time of day. In some embodiments, methods further comprise administering a treatment and/or taking treatment steps to address a condition causing or resulting from the chronopathology.

In some embodiments, provided herein are methods of chronotherapy, comprising: (a) determining the biological time-of-day of a subject using the methods herein; and (b) delivering a therapy or therapeutic at the appropriate or optimal biological time for the subject. In some embodiments, the chronotherapy is used to treat asthma, allergic rhinitis, cancer, cardiovascular disease, osteoarthritis, peptic ulcers, diabetes, arthritis, inflammatory conditions, autoimmune disease, etc.

In some embodiments, provided herein are systems or panels of biomarkers consisting of an isolated set of 500 or fewer (e.g., <400, <300, <200, <100, <50) cDNA biomarkers, wherein said isolated set includes two or more cDNA biomarkers from Table 1. In some embodiments, said isolated set includes 10 or more cDNA biomarkers from Table 1. In some embodiments, said isolated set includes 2 or more cDNA biomarkers selected from CLEC10A, PER1, GHRL, IL1B, NR1D1, DDIT4, GNG2, LLGL2, NR1D2, CD1C, DHRS13, GPCPD1, TIAM2, CD38, GZMB, ZNF438, EPHX2, and PDK1 cDNA biomarkers. In some embodiments, said isolated set includes the cDNA biomarkers CLEC10A, PER1, GHRL, IL1B, NR1D1, DDIT4, GNG2, LLGL2, NR1D2, CD1C, DHRS13, GPCPD1, TIAM2, CD38, GZMB, ZNF438, EPHX2, and PDK1. In some embodiments, the cDNA biomarkers comprise an exon-exon junction. In some embodiments, the cDNA biomarkers are full-length cDNA biomarkers.

DETAILED DESCRIPTION

Figure 1:
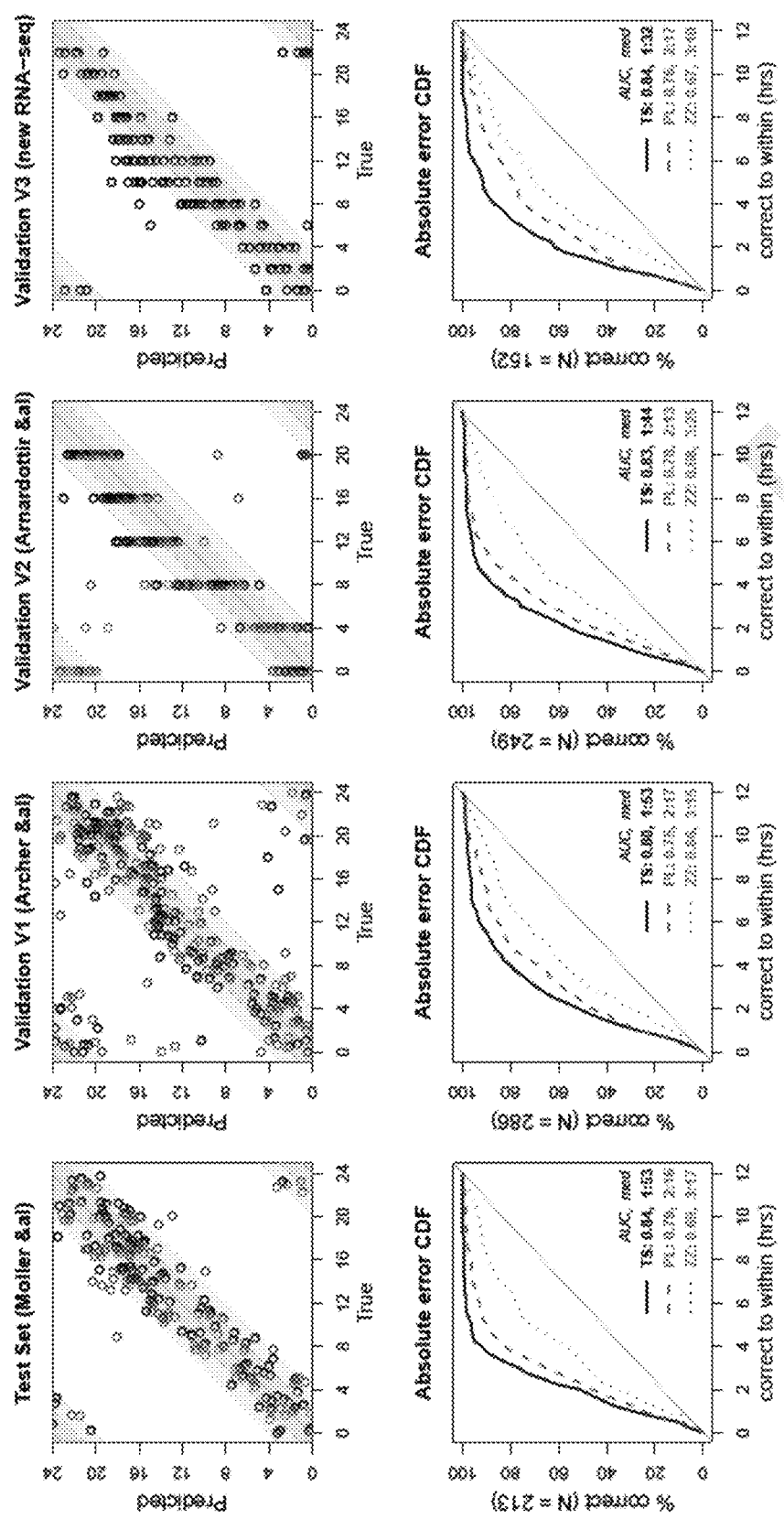
FIG. 1. Accuracy of an exemplary method applied to data from four distinct studies. Each column corresponds to the indicated dataset. The exemplary predictor was trained on a subset of subjects from the Möller-Levet study (Ref. 27; herein incorporated by reference in its entirety) and then applied to the remaining subjects (Test Set) along with three independent datasets: V1 (28), V2 (29), and V3. In the top row, the predicted time of day vs. true time of day for each sample is shown. Dark and light grey bands indicate an error range of ±2 and ±4 about the true time. For the first three studies, color of the point indicates experimental condition: in the Test Set, control vs. sleep restriction; in V1, control vs. forced desynchrony; in V2, control days, sleep deprived day, recovery day. In V3, color indicates individual subjects (n=6). In the bottom row, the fraction of correctly predicted samples for each study vs. the size of the error for the predictor is plotted (solid black), PLSR-based model (dashed), and ZeitZeiger (dotted). Normalized AUCs and median absolute errors are listed for each.

Provided herein are biomarkers of endogenous biological time (e.g. circadian time). In particular compositions and methods are provided for assessing the biological time of a subject, and diagnosis of diseases/conditions and/or providing treatments based thereon.

In some embodiments, provided herein are biomarkers (e.g., blood biomarkers) and biomarker signatures that reveal endogenous biological time and the underlying organization (e.g., on the 24 hour circadian clock of a subject). In some embodiments, methods are providing for assessing the biological time of a subject, (e.g., from a single blood draw). In some embodiments, panels of biomarkers are provided (e.g., panels of full length cDNAs). In some embodiments, analysis of the biomarkers herein (e.g., blood biomarkers) reflects the state of endogenous clocks in blood immune cells. In some embodiments, analysis of the biomarkers herein (e.g., blood biomarkers) reveal the temporal organization of organ systems, including the brain. In some embodiments, the technology herein provides for diagnosis of disrupted circadian rhythms and sleep in a wide range of human diseases. In some embodiments, the compositions and methods herein are useful in, for example, accurate diagnosis of circadian disruption in human disease, assessment of circadian disruption as a diagnostic or prognostic factor in disease progression or treatment response, application to the appropriate timing of therapeutic delivery (e.g., chronotherapy), etc.

In some embodiments, circadian time is accurately assessed across technical platforms using two blood samples (e.g., timed blood samples) from a single individual. This represents a significant improvement over other methods that require: (i) repeated sampling of individual analytes (such as melatonin), (ii) multiple samples from a single individual to assess timing from any single sample, and/or (iii) have not been validated across independent studies and technical platforms.

In some embodiments, provided herein are biomarker signatures (e.g., an up to 41-gene biomarker signature) and computational algorithms to accurately assess circadian time from a blood sample. In some embodiments, expression levels from each gene in the biomarker signatures (e.g., an up to 41-gene biomarker signature) o are expressed as the fold change from their mean expression over time on a per-subject basis ("within-subject renormalization"), allowing measurements from different individuals, studies, or platforms to be compared on a common scale. In experiments conducted during development of embodiments herein, data from was used to train the predictor and identify a biomarker signature (e.g., a 41-gene signature, subsets of the 41-gene signature, additional genes, etc.) using a machine learning algorithm ("periodic elastic net") that predicts circadian time as a function of gene expression. The resulting biomarker signatures are directly applied to data from new patients using two blood draws (e.g., spaced 8 (or more) hours apart (e.g., 8 hours, 9 hours, 10 hours, 11 hours, 12 hours, 13 hours, 14 hours, 15 hours, 16 hours, etc.).

Based on tests using data from four independent studies, embodiments herein are more accurate and efficient than competing methods, estimating circadian time to within 2 h for the majority of samples. The predictors herein are universally applied to yield highly accurate results in new data from other studies independent of differences in patient protocol or assay platform (without renormalizing the data or retraining the machine, and without artificially constraining the quantitation platform to a specific microarray or kit). This feature is unique amongst expression-based predictors, and addresses a major challenge in the development of generalizable and practical biomarker tests.

Circadian clocks play a key role in regulating a vast array of biological processes, with significant implications for human health. Accurate assessment of circadian function using transcriptional biomarkers found in human blood significantly improves diagnosis of circadian disorders and optimizes the delivery time of therapeutic treatments. To be useful, a test should be accurate, minimally burdensome to the patient, and readily generalizable to new data. A major obstacle in development of gene expression biomarker tests is the diversity of measurement platforms and the inherent variability of the data, often resulting in predictors that perform well in the original datasets but cannot be universally applied to new samples collected in other settings. Provided herein are algorithms that robustly infers circadian time from collected samples (e.g., human blood samples). Experiments conducted during development of embodiments herein demonstrate application of the predictor/algorithm in data from three independent studies using distinct microarrays, and further validate it against a new set of samples profiled by RNA-Seq. Results show that the exemplary predictor/algorithm is more accurate and efficient than competing methods, estimating circadian time to within 2 h for the majority of samples. Experiments conducted during development of embodiments herein demonstrate that once trained on data from a single study, the resulting predictor is universally applicable to yield highly accurate results in new data from other studies, independent of differences in study population, patient protocol, or assay platform without renormalizing the data or retraining the machine. This feature is unique amongst expression-based predictors, and addresses a major challenge in the development of generalizable, clinically-useful tests.

Circadian clocks drive a vast repertoire of periodic biochemical, physiological, and behavioral processes in organisms from bacteria to humans. Whereas these processes were previously assumed to be driven by the sleep-wake cycle and hormonal cues, recent molecular genetics research has uncovered a complex network of biochemical interactions that regulate circadian function in virtually every organ. Genetic studies in the fruit fly, mouse, and humans have revealed an evolutionarily conserved mechanism driven by the oscillatory activation and repression of core clock genes (e.g., Clock, Bmal1, Per1-3, and Cry1-3) (Refs. 1, 2; herein incorporated by reference in their entireties). In mammals, this system in turn regulates the expression for nearly half the genome (Ref. 3; herein incorporated by reference in its entirety), transmitting temporal information to coordinate cellular processes. These hundreds of rhythmic genes exhibit diurnal expression peaks in many organs at various times throughout the day, reflecting time-of-day specific functions in different tissues.

Abundant epidemiological evidence links circadian regulation to human health. Environmentally-induced circadian disruption, including the familiar travel-induced experience of jet lag (Ref. 4; herein incorporated by reference in its entirety) and the more chronic phenomenon of "social jet lag" experienced by those whose daily schedules of work and life are out of sync with their internal clock (Refs. 5, 6; herein incorporated by reference in their entireties), are known to increase injury and disease risk (Refs. 6-9; herein incorporated by reference in their entireties). An estimated 50% of adults suffer from social jet lag, including over 8 million shift workers in the United States alone (Ref. 6; herein incorporated by reference in its entirety); if sufficiently disruptive, misalignment between sleep and the 24-hour social and physical environments can lead to circadian sleep/wake cycle disorders, in which individuals complain of insomnia and daytime sleepiness (Ref. 5; herein incorporated by reference in its entirety). Moreover, it is now understood that genetic variations contribute strongly toward an individual's preferred sleep timing and predisposition to circadian misalignment (Ref. 10-12; herein incorporated by reference in their entireties); for instance, mutations in PER and CK1δ have been linked to a familial form of advanced sleep phase syndrome, in which affected individuals sleep and wake much earlier than their unaffected siblings (Refs. 13-15; herein incorporated by reference in their entireties). Sleep disruption is associated with increased risk of cardiovascular disease, diabetes, and obesity (Refs. 8, 10, 16; herein incorporated by reference in their entireties). It has also been observed to be a symptom of neurodegenerative disease and traumatic brain injury (Ref. 17; herein incorporated by reference in its entirety). Recently, the emerging field of chronopharmacology has established links between the timing of delivery and the effectiveness/tolerance of treatment (Ref. 9, 16; herein incorporated by reference in their entireties). Together, this body of evidence indicates that assessments of clock function are valuable for disease risk prediction, diagnostic assays, and refined treatment protocols.

These observations have motivated a growing interest in using measurements of circadian regulation in the clinic. Although a number of measures are currently used to assay human circadian clocks in a clinical setting (e.g., melatonin, cortisol, core body temperature, actigraphy, core clock gene expression, etc.) (Ref. 18; herein incorporated by reference in its entirety), they suffer shortcomings that limit their utility. The major limitation of these techniques is the need for serial sampling over extended periods of at least 24 hours, which is both costly and burdensome to the patient. Experiments conducted during development of embodiments herein elucidated that the clock gene program is present in almost all tissues, including peripheral blood mononuclear cells (PBMC), indicating the existence of cell-autonomous clocks and offers an alternative approach for circadian assessment. These peripheral clocks are synchronized with the neural pacemaker in the hypothalamic suprachiasmatic nucleus (SCN) (Ref. 19; herein incorporated by reference in its entirety), which drives rhythmic expression of the pineal hormone melatonin and adrenal cortisol, as well as body temperature and feeding rhythms. Changes in gene expression in PBMC correlates with habitual sleep-wake timing, consistent with the notion that PBMC rhythms are reset by the circadian pacemaker the SCN, which also drives circadian sleep-wake changes (Ref. 20; herein incorporated by reference in its entirety). Peripheral clocks thus serve as an indicator of the circadian state in the brain. The development of an assay from a small number of blood draws would thus represent a major step forward, facilitating assessments of circadian disruption in a range of conditions. A promising approach for such an assay would be to use transcriptional profiling of PBMC to detect circadian rhythms by using variations in gene expression as indicator of circadian state. Yet, while identifying molecules whose expression varies periodically with the circadian cycle has been the focus of multiple studies (Refs. 21, 22; herein incorporated by reference in their entireties), the inverse problem of attempting to infer circadian time from a set of transcriptomic markers has received comparatively little attention. From an analytical standpoint, one challenge is a machine learning problem: that of predicting the value of a periodic variable (time of day) from variations in a high-dimensional feature space (gene expression). To be clinically useful, such a predictor should ideally have three major capabilities. (1) yield highly accurate predictions in human subjects (e.g., not simply in model organisms under strictly controlled conditions) with enough precision that a clinically relevant shift in an individual's circadian rhythm is reliably inferred from the difference in the predicted and true time of day; (2) yield predictions using a minimal number of samples from the tested individual (so as to minimize the invasiveness of the test) with a parsimonious set of markers (e.g., tens rather than thousands of genes) both to ensure feasibility and reduce noise; (3) the predictor should be insensitive to differences in sample processing or assay technologies (e.g., different microarray platforms, RNA-Seq, RT-PCR, etc.), including platforms that differ from the training data, to ensure its generalizability. No method proposed for this purpose to date has achieved all the above capabilities.

The Molecular Timetable method (Ref. 23; herein incorporated by reference in its entirety), which uses the peak expression times of a complement of ~50 genes to assess circadian time, is highly inaccurate when applied to human data (Refs. 24, 25; herein incorporated by reference in their entireties). The machine-learning based ZeitZeiger method (Refs. 24, 26; herein incorporated by reference in their entireties) improves upon the accuracy of Molecular Timetable, but cannot be applied to a new sample without retraining the entire machine, thus sacrificing reproducibility and interpretability (since in effect each new subject will have a different predictor). A more recent PLSR-based method (Ref. 25; herein incorporated by reference in its entirety) also exhibits improved accuracy, but requires assaying a complement of ~26,000 transcripts in order to perform the first normalization and standardization step necessary to apply the 100-gene PLSR model.

Most critically, none of the algorithms proposed to date has established that a predictor trained in one set of human samples can accurately generalize to a completely new dataset, which may exhibit different characteristics from the training data that cannot be accounted for when fitting the model. In all cases (Refs. 23-26; herein incorporated by reference in their entireties), when separate datasets were used, they were first combined and co-normalized (and, in some cases, constrained to follow the same protocol and platform) before being separated into training and testing subsets. Because the validation data in these studies did not comprise independent external samples, the generalizability and reproducibility is questionable.

Demonstrating the ability of the predictor to generalize to external datasets is crucial in two ways. First, it ensures that the predictor is not sensitive to systematic differences between the training data and the dataset used in the prediction. When the disparate datasets are combined before being redivided into training and testing subsets, it creates an artificial expectation that the testing data statistically resembles the training data in a manner that is unrealistic in practice (e.g., in which new patients would comprise a distinct batch). Second, it ensures that the predictor remains relevant even as new assay technologies are developed; a model that was devised using microarray data, for example, should remain accurate when applied to RNA-Seq data if the underlying signal is biologically relevant.

In some embodiments, provided herein is a machine learning approach that yields precise predictions of time-of-day from human blood transcriptomic data. The predictors/algorithms herein use a unique within-subject normalization procedure that is well-suited to circadian profiling and reduces the variability between studies without requiring common experimental platforms, batch correction, or retraining the machine to account for cross-study variability. In some embodiments, provided herein is a predictor comprising ~40 genes (or a subset thereof, or a panel comprising all or a portion of the ~40 genes plus additional genes, etc.), which are assayed using any quantitation method. The predictor/algorithm maintains high accuracy when applied to completely separate validation datasets, including those using different microarray platforms and RNA-Seq. The result is a time-prediction algorithm that is efficient, accurate, and generalizable.

Experiments were conducted during development of embodiments herein to demonstrate to apply an exemplary predictor/algorithm to public data from a microarray study quantifying the human blood transcriptome over the circadian cycle (Ref. 27; herein incorporated by reference in its entirety), and then validated it using three independent datasets: two other public microarray studies (Refs. 28, 29; herein incorporated by reference in their entireties) as well as new data from eleven additional healthy subjects profiled by RNA sequencing (RNA-seq). All studies were able to predict the time of day of samples with a median error rate of under two hours in human patients. Samples from these datasets that corresponded to sleep-disrupted conditions (e.g., sleep deprivation (Refs. 27, 29; herein incorporated by reference in their entireties) or forced desynchrony (Ref. 28; herein incorporated by reference in its entirety)) exhibited larger discrepancies between the "blood time" detected and the "clock time" at which the sample was drawn, suggesting that the difference in the signature and the clock time may be a useful diagnostic for sleep disruption. Results obtained using the exemplary predictor/algorithm herein with competing methods (Refs. 23, 26; herein incorporated by reference in their entireties) demonstrate that the biomarkers and methods herein significantly outperform other methods in efficiency, accuracy, and generalizability.

A key feature of the systems and methods herein is its consistent accuracy across study protocols, patient conditions, and transcriptomics platforms. Once trained on microarray data from a single public circadian expression profiling study, the predictor is applied with high accuracy to data from other studies using different microarray platforms or RNA-seq without renormalizing the data or re-training the machine. This capability is exceptional in the context of omics analyses, where the systematic variation of "batch effects" often overwhelms the signal of interest. The robust signal detection, even across distinct studies and platforms, supports the notion that the pattern of circadian gene expression being detected by the algorithm is strong and highly reproducible. The generalizability of the predictor is also an extremely useful feature from a practical standpoint, making the predictors/algorithms within the scope herein useful diagnostic tools.

Exemplary Predictor/Algorithm

The basic framework consists of a rescaling/normalization step, fitting the predictor using the training data, and applying it to predict time-of-day in new samples from disparate studies.

1. Within-Subject Renormalization.

In order to ensure that the predictor is applied to high-throughput gene expression profiling data independently of the measurement platform used, it is necessary to ensure that the data are expressed on a consistent and unitless scale. To this end, the gene expression measurements are first $\log_2$ transformed (as is customary for transcriptomic data), such that a unit increase in gene expression values within each study considered represents a doubling in mRNA abundance. The ($\log_2$) expression of gene j in sample i is denoted as $x_{ij}$, where sample i corresponds to a measurement from subject $s_i$ taken at time $t_i$. Next, for each subject in each study, the mean $\log_2$ expression level of each gene is computed across all assayed timepoints for that subject over the circadian cycle, and the data for each gene is centered about its timecourse mean on a per subject basis:

$$z_{ij} = x_{ij} - \frac{\sum_{k=1}^{N} \mathbb{1}_{s_k=s_i} x_{ij}}{\sum_{k=1}^{N} \mathbb{1}_{s_k=s_i}}. \qquad [1]$$

The resulting renormalized value $z_{ij}$ thus represents the foldchange deviation of gene j at time $t_i$ from its mean over time in subject $s_i$. Equivalently, $z_{ij}$ is the log of the ratio of the raw mRNA measurement to its geometric mean; it is therefore a unitless quantity, and hence independent of the original assay platform.

In some embodiments, each subject has expression data for at least two timepoints, and that these timepoints are sufficiently spaced in time such that the second term of Eq. 1 represents a valid summary of the average expression of gene j over the course of a day (e.g., separated by 2 hours, 3 hours, 4 hours, 5 hours, 6 hours, 7 hours, 8 hours, 9 hours, 10 hours, 11 hours, 12 hours, or ranges therebetween).

2. Fitting the Periodic Elastic Net Predictor.

Having transformed the training data as described above, a multivariate regression model with elastic net regularization (Ref. 30; herein incorporated by reference in its entirety) is fit to predict sinusoidal functions of the time of day as a function of the transformed gene expression data. Specifically, a bivariate regression is performed on the cartesian coordinates corresponding to the angle of the hour hand on a 24-hour clock, $$Y_{(N \times 2)} = \begin{bmatrix} \sin(2\pi t_i / 24) \\ \cos(2\pi t_i / 24) \end{bmatrix}^T = \beta_0 + Z_{(N \times p)} \beta_{(p \times 2)} + \eta_{(N \times 2)}, \qquad [2]$$

where $t_i$ denotes the time of day for observation i, Z is the N (observations) by p (genes) matrix of predictors after the transformation described in Eq. 1, and follows a bivariate normal distribution. (N denotes the number of observations, not the number of subjects; e.g., if there are n subjects each with a time-series comprising m blood-draws, the total number of observations is N=nm).

The number of possible biomarkers far outstrips the number of observations; the vast majority of assayed genes will not be strongly predictive of time. In order to reduce overfitting and obtain a parsimonious model, elastic net regularization (Ref. 30; herein incorporated by reference in its entirety) is used for feature selection. Rather than computing a least-squares fit to Eq. 2, the penalized problem is solved:

$$\min_{(\beta_0,\beta) \in \mathbb{R}^{(p+1) \times 2}} \left[ \frac{1}{2N} \sum_{i=1}^{N} \|\vec{y_i} - \beta_0 - \beta^T \vec{z_i}\|_F^2 + \lambda \left( (1-\alpha) \|\beta\|_F^2 / 2 + \alpha \sum_{j=1}^{p} \sqrt{\beta_{j1}^2 + \beta_{j2}^2} \right) \right], \quad [3]$$

where $\sim z_i$ is a p-dimensional column vector containing the full gene expression profile for sample i; $\sim y_i$ is the 2-dimensional vector of sine and cosine time terms derived from $t_i$ (the time at which the $i^{th}$ sample was taken); $\beta_{j1}$ and $\beta_{j2}$ correspond to the entries in the $j^{th}$ row of the matrix (representing the coefficient for gene j modeling the sine and cosine time terms, respectively); and $\|\cdot\|_F$ denotes the Frobenius norm.

In Eq. 3 the first term corresponds to the usual total least squares fit, while the second term assigns a penalty, tuned by $\lambda$, that goes as the norms of the regression coefficients. The effect of the penalty terms is to shrink the $\beta$ coefficients toward 0, ultimately removing predictors from the model if the improvement to the least squares fit produced by keeping them does not adequately compensate the penalty. The parameter $\lambda$ governs the stiffness of the penalty, and hence the degree of shrinkage; larger values of $\lambda$ will produce more parsimonious models. In practice, both $\lambda$ and $\alpha$ (which governs the trade-off between the Frobenius and $L_2$ group norm penalty) are tuned by cross-validation (Ref. 30; herein incorporated by reference in its entirety).

It can be seen from the second ($L_2$) penalty term in Eq. 3 that a group lasso penalty is applied to each pair of coefficients $(\beta_{j1}, \beta_{j2})$, indicating that the gene's influence on both the sine and cosine time terms are considered simultaneously. This has the appealing property of yielding sparsity in the overall model while limiting sparsity within the group; when=1, the group lasso penalty implies that a given gene j will have non-zeros for either both the sine and cosine time functions, or neither (Ref. 31; herein incorporated by reference in its entirety).

Predicting Time-of-Day and Assessing Accuracy

Once the coefficients are fit, predictions for the time-of-day may be estimated from the above model using the four-quadrant inverse tangent as $$\hat{t}_i = \frac{24}{2\pi}(\text{atan2}(\hat{y}_{i1}, \hat{y}_{i2}) \mod(2\pi)), \quad [4]$$

where the modulo is used to ensure that the conversion from angle to time ranges on [0, 24). Predictions are then compares to the true time-of-day for sample i to assess the prediction accuracy. Of interest is the number of hours by which the prediction is off, modulo whole days. It is thus computed:

$$\epsilon_i = \min(|\hat{t}_i - t_i|, 24 - |\hat{t}_i - t_i|) \quad [5]$$

to assess the prediction error for a sample i, where the min(·) function ensures that a 23-hour difference is treated as a 1-hour difference. This may be thought of as the angular error, in hours, of the predicted time-of-day. It bears observing that the by values predicted by Eq. 2 are not guaranteed to lie on the unit circle (where the true response data lie), and that in fitting Eq. 3 it is sought to minimize the square of the total error. This is given in Cartesian coordinates as the first term of Eq. 3, and this will also minimize the combined angular and radial errors as the Frobenius norm is invariant under orthogonal transformation. Assessing the accuracy via Eqs. 4-5 concerns only with the angular component, disregarding the radial error. Eqs. 2-3 are fit to minimize the total error (allowing the use of standard multivariate regression tools) and as a soft constraint keeping the prediction close to the unit circle).

Methods to accurately assess the state of an organism's internal clock are useful in understanding the role of circadian rhythms in biological processes, diagnosing circadian disruption, and targeting chronotherapeutics. To be practically useful, such a method should be robust enough to withstand variability amongst individuals and clinics, and should minimize the burden on the patient. The predictors/algorithms achieve these goals by training a supervised machine learning algorithm to "learn" the time-of-day as a function of gene expression in blood. Once trained, the model is applied to new gene expression data to yield predictions that reflect the internal state of the subjects' biological clock. Experiments conducted during development of embodiments herein demonstrated that the predictor/algorithm provides time predictions to within 2 h in human data, achieving considerably higher accuracy than competing methods in the same data. The high accuracy is achieved using a minimal number of markers (e.g., a panel comprising 40 biomarkers, a panel comprising 18 biomarkers, etc.), providing a simple and affordable diagnostic test.

Embodiments herein avoid the problems of cross-study renormalization by relying instead on within-subject renormalization. Centering the data for each subject about the daily mean for that gene in that subject, not only remove batch effects, but individual differences in baseline gene expression as well; in effect, removing any "DC" differential expression, such that the model considers only the time-varying part. Since any systematic contribution to the gene expression affects all time-points equally, the fold-changes from the mean is independent of batch, platform, or any other external factors. Moreover, because this scheme removes not only batch effects, but also any baseline subject-to-subject variation, a source of noise in the prediction is removed.

This scheme is effective because the signal relevant to inferring circadian time is the fluctuation about the mean of oscillating genes. In contexts where the mean gene expression is the signal of, the within-subject renormalization presented herein removes the variable of interest. As such, the within-subject renormalization is well-suited to modeling cyclic behaviors such as circadian rhythms.

In some embodiments, within-subject normalization is readily applied to new data, without manipulating the other data (including the training set) or the trained predictor in any way. In some embodiments, within-subject normalization utilizes at least two samples (blood draws) from a given subject so that the diurnal mean is estimated. Two timepoints are sufficient to apply the predictor/algorithm to a new subject with equally high accuracy as that obtained from more samples. While spacing the samples 12 hours apart may be ideal, a spacing of, for example, 10 or 8 hours yields highly accurate results. This permits great flexibility in scheduling patients for the two blood draws.

Approaches that rely on cross-normalization (e.g., ZeitZeiger or the Molecular Timetable method) can only be applied to predict time of day from a single blood-draw only when that sample was already part of the original dataset, since cross-normalization with the training data requires that there be at least two samples (and ideally many more) in the "batch" comprising the data from the new patient. As such, these alternative approaches are unable to overcome the need for multiple samples. Although the PLSR-based method is able to make single-draw predictions, it achieves this by using genome-wide z-scoring to calibrate the predictors, requiring thousands more genes to be assayed than are used in the model, and likewise exhibits substantially better performance when two samples with a 12 h separation are provided.

Analysis Methods

In some embodiments, provided herein are systems, methods, an algorithms for detecting the circadian state (e.g., any biological time) of a subject by detecting the level of various biomarkers (e.g., one or more of the biomarkers of Table 1) in a sample (e.g., blood sample, processed blood sample, other biological sample) from the subject. In some embodiments, methods are provided for detecting the level of expression of circadian biomarkers (e.g., one or more of the biomarkers of Table 1). The biological sample can include, for example, cells, tissue (e.g., a tissue sample obtained by biopsy), blood, serum, plasma, urine, sputum, cerebrospinal fluid, lymph tissue or fluid, or pancreatic fluid. In particular embodiments, the sample is blood or a blood product (e.g., serum, plasma, etc.) from the subject.

In some embodiments, methods are provided for RNA extraction and biomarker expression measurement. In some embodiments, RNA is extracted using, e.g., Trizol Reagent from Invitrogen following manufacturer's instructions, and detected directly or converted to cDNA for detection. RNA may be amplified using, e.g., MessageAmp kit from Ambion following manufacturer's instructions. Amplified RNA may be quantified using, e.g., HG-U133A or HG-U133_Plus2 GeneChip from Affymetrix Inc. or a compatible apparatus, e.g., the GCS3000Dx GeneChip System from Affymetrix Inc., using the manufacturer's instructions. The resulting biomarker expression measurements may be further analyzed as described herein.

In some embodiments, one or more of the biomarkers provided herein (e.g., of Table 1) may be measured in a biological sample (e.g., a blood sample) obtained from a subject (e.g., a subject suspected of suffering from desychrony, sleep deprivation, a disease or condition cause by sleep issues, a disease or condition causing sleep issues, etc.) using, e.g., polymerase chain reaction (PCR), reverse transcriptase PCR (RT-PCR), quantitative real-time PCR (qRT-PCR), an array (e.g., a microarray), a genechip, pyrosequencing, nanopore sequencing, sequencing by synthesis, sequencing by expansion, single molecule real time technology, sequencing by ligation, microfluidics, infrared fluorescence, next generation sequencing (e.g., RNA-Seq techniques), Northern blots, Western blots, Southern blots, NanoString nCounter technologies, proteomic techniques (e.g., mass spectrometry or protein arrays), and combinations thereof.

In some embodiments, devices are provided for detecting the level of expression of one or more biomarkers shown in Table 1. The device may include at least one single-stranded nucleic acid (e.g., a probe) having at least 85% sequence identity (e.g., 85%, 90%, 95%, 97%, 98%, 99%, or 100% sequence identity) to a nucleic acid sequence that is complementary or identical to at least 5 (e.g., at least 10, at least 15, at least 20, or more) consecutive nucleotides of one or more biomarkers shown in Table 1, in which the at least one single-stranded nucleic acid is sufficient for the detection of the expression level of the one or more biomarkers. The device may be used to detect the expression level of a given biomarker by specific hybridization between the single-stranded nucleic acid and the biomarker (e.g., an mRNA, genomic DNA, or non-coding RNA), a nucleic acid encoding the biomarker (e.g., an mRNA), or a complementary nucleic acid thereof. The device may be or include a microarray. The device may also include or be used with reagents and materials for next generation sequence (e.g., sequencing by synthesis). The device may also include or be used with NanoString reagents and at least one nCounter cartridge. The device may be or include a protein array, which contains one or more protein binding moieties (e.g., proteins, antibodies, nucleic acids, aptamers, affibodies, lipids, phospholipids, small molecules, labeled variants of any of the above, and any other moieties useful for protein detection as well known in the art) capable of detectably binding to the polypeptide product(s) of one or more biomarkers shown in Table 1. The device may also be a cartridge for measuring an amplification product resulting from hybridization between one or more nucleic acid molecules from the patient and at least one single-stranded nucleic acid single-stranded nucleic acid molecules of the device, such as a device for performing qRT-PCR.

The expression levels of the biomarkers (e.g., the biomarkers listed in Table 1 may be determined using high-throughput expression profiling platforms, such as microarrays. In particular, a microarray contains or is produced by generating oligonucleotide probes (e.g., DNA, cDNA, or RNA probes) capable of hybridizing to one or more biomarkers of interest (e.g., one or more of the biomarkers of Table 1) or the complement sequences thereof. Each probe can have, e.g., at least 10, 15, 20, 25, 30, or more contiguous nucleic acid residues (e.g., at least 15) that are complementary or identical to a nucleic acid sequence of a selected biomarker. The probe nucleic sequence can also have at least 85% (e.g., 90%, 95%, 99%, or 100%) sequence identity to the nucleic acid sequence of the gene coding the biomarker or the complement sequence thereof. In particular, the probe sequences can be complementary to all or a portion of the nucleic acid sequence of the biomarker(s).

A microarray probe may be single-stranded or double-stranded. The probe may be labeled (e.g., detectably labeled with a fluorescent molecule, dye molecule, small molecule, epitope tag, barcode sequence, polypeptide, or any other detectable molecule). Probes can be detectably labeled and immobilized on a solid support to form the microarray. For example, probes can be either prefabricated and spotted to the surface or directly synthesized on to the surface (in situ) of the microarray. The microarray can also be configured such that the sequence and position of each member (e.g., probe) of the array is known. Hybridization of a labeled probe with a particular target nucleic acid (e.g., an mRNA corresponding to one or more biomarkers of Table 1) indicates that the sample from which the mRNA was derived expresses that biomarker. In some embodiments, such methods are used to quantitate the level of the biomarkers.

In some embodiments, PCR-based techniques are used to determine the level of one or more biomarkers (e.g., one or more biomarkers of Table 1) in a sample. Samples from a subject can be conveniently assayed for gene expression levels using polymerase chain reaction (PCR) analysis, such as quantitative real-time PCR (qPCR), or quantitative loop-mediated isothermal amplification (q-LAMP). For example, an mRNA corresponding to a biomarker of Table 1 can be detected in a biological sample by (a) producing cDNA (e.g., full-length cDNA, cDNA spanning an exon-exon junction) from the sample by reverse transcription using at least one primer; (b) amplifying the cDNA so produced using a target polynucleotide as sense and antisense primers to amplify target cDNAs therein; and (c) detecting the presence of the amplified target cDNA using polynucleotide probes. The primers and probes may be used to detect expression of one or more of the indicated biomarkers using PCR. The methods can include one or more steps that allow determination of the levels of target mRNA in a biological sample (e.g., by simultaneously examining the levels of a comparative control mRNA sequence or "housekeeping" gene, such as an actin family member or GAPDH). The primers for these PCR-based assays may be labeled for detection according to methods known in the art.

In some embodiments, sequencing techniques are used to determine the level of one or more biomarkers (e.g., one or more biomarkers of Table 1) in a sample. In some embodiments, the expression levels of the biomarkers shown in Table 1 may be determined using sequencing technologies, such as next generation sequencing platforms (e.g., RNA-Seq), as described in Mortazavi et al., Nat. Methods 5: 621-628, 2008, hereby incorporated by reference. RNA-Seq is a robust technology for monitoring expression by direct sequencing of the RNA molecules in a sample. This methodology may include fragmentation of RNA to an average length of, e.g., 200 nucleotides, conversion to cDNA by random priming, and synthesis of double-stranded cDNA (e.g., using the PROTOSCRIPT®. First Strand cDNA Synthesis Kit from New England Biosciences). The cDNA may then be converted into a molecular library for sequencing by addition of sequence adapters for each library (e.g., from ILLUMINA/Solexa), and the resulting 50 to 100 nucleotide reads are mapped onto the genome. Exemplary sequencing platforms suitable for use according to the methods include, e.g., pyrosequencing, ILLUMINA sequencing by synthesis, SOLID sequencing, ION TORRENT sequencing, SMRT sequencing, and others.

In some embodiments, various methods of quantifying the biomarker level in a sample comprise the generation of biomarker cDNA. In some embodiments, provided herein are systems, compositions, or panels comprising two or more (e.g., 2, 3, 4, 5, 6, 7, 8, 9, 10, 15, 20, 25, 30, 35, 40, 45, 50, 60, 70, 80, 90, 100, 110, 120, 130, 140, 150 or ranges therebetween) cDNAs corresponding to the biomarkers described herein (e.g., of Table 1). In some embodiments, the system comprises 10 or more (e.g., 10, 20, 30, 40, 50, 75, 100, 200, or more, or ranges therebetween) cDNAs. In some embodiments, the system comprises fewer than 1000 cDNAs (e.g., 1, 2, 5, 10, 25, 50, 100, 200, 300, 400, 500, 600, 700, 800, 900, 1000, or ranges therebetween (e.g., fewer than 200, fewer than 50, etc.). In some embodiments, a cDNA is a full-length cDNA (e.g., comprising a DNA sequence corresponding to the full mRNA sequence encoding a particular biomarker). In some embodiments, a cDNA encompasses an exon-exon junction. In some embodiments, a cDNA is conjugated or tethered to a solid surface (e.g., chip, bead, etc.). In some embodiments, a cDNA is free in solution. In some embodiments, a cDNA is not naturally occurring.

In some embodiments, a computer-based analysis program is used to translate the raw data generated by the detection assay (e.g., the presence, absence, or amount of expression a panel of genes) into data of predictive value for a clinician (e.g., a risk score, a qualitative description, etc.). In some embodiments, computer analysis combines the data from numerous biomarkers into a single score or value that is predictive and/or diagnostic. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information providers, medical personal, and subjects. For example, in some embodiments of the present invention, a sample (e.g., blood or serum sample) is obtained from a subject and submitted to a profiling service (e.g., clinical lab at a medical facility, third-party testing service, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

In some embodiments, profile data is prepared in a format suitable for interpretation by a treating clinician. For example, rather than providing raw expression data, the prepared format may represent a diagnosis for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, a report is generated (e.g., by a clinician, by a testing center, by a computer or other automated analysis system, etc.). A report may contain test results, diagnoses, and/or treatment recommendations.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease.

In some embodiments, all or a portion of the methods described herein are provided as a service. In some embodiments, a user (e.g., subject (e.g., patient), clinician, researcher, etc.) arranges, contracts, pays, etc. to have a sample (e.g., biological sample (e.g., blood product, etc.), nucleic acid sample, etc.) and/or data (e.g., raw data) analyzed. In some embodiments, a sample is submitted (e.g., in-person, via mail or courier, etc.) and analysis of the sample for specific biomarkers described herein (alone or with other biomarkers is performed by the service (e.g., at a diagnostic testing facility, etc.). In some embodiments, data collected by a user (e.g., a clinician, researcher, etc.) are submitted to a testing facility for analysis. Embodiments described herein include any suitable combination of user-performed (e.g., subject-performed, clinician-performed, etc.) and service-performed steps. In some embodiments, methods described herein comprise of consist of only the steps performed by either the user (e.g., subject, clinician, etc.) of the service (e.g., sample collection, sending a sample, sample analysis, data collection, data analysis, receiving a report, etc.), or the service (e.g., sample collection, receiving a sample, sample analysis, data analysis, generating a report, sending a report, etc.). In some embodiments, any combination of steps may be performed by a user and/or service.

In some embodiments, analysis results are reported (e.g., to a health care professional, to a subject, etc.). In some embodiments, a result is provided on a peripheral, device, or component of an apparatus. For example, sometimes an outcome is provided by a printer or display. In some embodiments, an outcome is reported in the form of a report, and in certain embodiments the report comprises biomarker levels, risk assessment, a compiled score (e.g., based on a plurality of markers), etc. An outcome can be translated into and displayed in a suitable format that facilitates downstream use of the reported information.

In some embodiments, generating and reporting results from the raw biomarker data comprises transformation of the data reads into a representation that reflects information not determinable in the absence of the method steps described herein. Converting biomarker levels into useful information allows actions to be taken.

In some embodiments, a user or a downstream individual, upon receiving or reviewing a report comprising one or more results determined from the analyses provided herein, will take specific steps or actions in response. For example, a health care professional or qualified individual may provide further testing of a subject. A public health official may take steps provide assistance to the subject. The present invention is not limited by the number of ways or fields in which the technology herein may find use.

The term "receiving a report" as used herein refers to obtaining, by a communication means, a written and/or graphical representation comprising results or outcomes of the biomarker analysis described herein. The report may be generated by a computer or by human data entry, and can be communicated using electronic means (e.g., over the internet, via computer, via fax, from one network location to another location at the same or different physical sites), or by another method of sending or receiving data (e.g., mail service, courier service and the like). In some embodiments, the outcome is transmitted in a suitable medium, including, without limitation, in verbal, document, or file form. The file may be, for example, but not limited to, an auditory file, a computer readable file, a paper file, a laboratory file or a medical record file. A report may be encrypted to prevent unauthorized viewing.

As noted above, in some embodiments, systems and method described herein transform data from one form into another form (e.g., from physical biomarkers in a sample to actual diagnosis, etc.). In some embodiments, the terms "transformed", "transformation", and grammatical derivations or equivalents thereof, refer to an alteration of data from a physical starting material (e.g., nucleic acid or protein in a biological sample, etc.) into a digital representation of the physical starting material (e.g., read data), a representation of the amount of that starting material (e.g., biomarker level), a condensation of the sequential representation (e.g., a combined signature based on multiple biomarkers), or a diagnosis, prognosis, or risk assessment, etc. In some embodiments, transformation involves conversion of data between any of the above.

Certain processes and methods described herein (e.g., data acquisition, data analysis, communication, etc.) are performed by (or cannot be performed without) a computer, processor, software, module and/or other device. Some methods described herein typically are computer-implemented methods, and one or more portions of a method sometimes are performed by one or more processors. In some embodiments, an automated method is embodied in software, processors, peripherals and/or an apparatus comprising the like. As used herein, software refers to computer readable program instructions that, when executed by a processor, perform computer operations, as described herein.

The terms "obtaining," "transferring," "receiving," etc. refer to movement of data (e.g., raw data, biomarker levels, combined biomarker data, risk profile, signature, diagnosis, etc.) between modules, devices, apparatuses, etc. within a system. These terms may also refer to the handling of samples and purified versions thereof (e.g., with respect to amplification, purification, analysis, etc.). Input information may be generated in the same location at which it is received, or it may be generated in a different location and transmitted to the receiving location. In some embodiments, input information is modified before it is processed (e.g., placed into a format amenable to processing (e.g., tabulated)). In some embodiments, provided are computer program products, such as, for example, a computer program product comprising a computer usable medium having a computer readable program code embodied therein, the computer readable program code adapted to be executed to implement a method.

Software may include one or more algorithms in certain embodiments. An algorithm (e.g., algorithms described herein) may be used for processing biomarker data, analyzing data, and/or providing an outcome or report according to a sequence of instructions. An algorithm often is a list of defined instructions for completing a task. Starting from an initial state, the instructions may describe a computation that proceeds through a defined series of successive states, eventually terminating in a final ending state. By way of example, and without limitation, an algorithm may be a search algorithm, sorting algorithm, merge algorithm, numerical algorithm, graph algorithm, string algorithm, modeling algorithm, computational genometric algorithm, combinatorial algorithm, machine learning algorithm, cryptography algorithm, data compression algorithm, parsing algorithm and the like. In some embodiments, an algorithm or set of algorithms transform data (e.g., biomarker) into information useful for solving a problem (e.g., identifying a subject as depressed or at-risk of depression). Algorithms utilized in embodiments herein make improvements in the fields of mental health, public health, medicine, diagnostic applications, diagnostic development, etc. In certain embodiments, algorithms may be implemented by software.

Experimental

Materials and Methods

Public data sources. Experiments were conducted during development of embodiments herein to analyze data from three independent studies comprising transcription profiling timecourses in human blood. Data were obtained from the NCBI Gene Expression Omnibus (GEO) repository (36) and imported into R using GEOquery (Ref. 37; herein incorporated by reference in its entirety) under the following accession numbers: GSE39445 (Ref. 27; herein incorporated by reference in its entirety), GSE48113 (Ref. 28; herein incorporated by reference in its entirety), GSE56931 (Ref. 29; herein incorporated by reference in its entirety). Details of the datasets may be found in Table 2. Data from eleven new subjects comprise the final dataset, V3. Recruitment and inclusion/exclusion criteria are described in the Supporting Information. Whole blood was collected every 2 h over a 28 h period (15 timepoints total) from each subject, yielding a total of 165 samples. Whole blood transcriptional profiling was carried out using RNA sequencing. Ten samples did not meet the RNA quality thresholds and were excluded from further analyses. RNA-Seq data for the remaining 152 samples were processed.

entirety) were used to train the TimeStamp machine following Eq. 3. Within this 24-timecourse training set, ten-fold CV was used to tune λ and α, selecting values that best minimized the OOB residuals. To obtain the "core" TimeStamp genes, this process was repeated 12 times using different subsets of GSE39445 for the training data. In all cases, the models with the optimal and retained ~40 genes, of which 18 appeared in at least 6 runs. Prediction accuracy was independent of the identity of the remaining "auxiliary" predictors, and thus a single representative run was chosen as the trained model.

Testing and Validation.

The trained model was then applied to the remaining 24 timecourses from GSE39445 (Ref. 27; herein incorporated by reference in its entirety) that had not been chosen to form the training set, providing a independent test of the model accuracy. In addition, it was also applied to three independent validation datasets: GSE48113 (28), GSE56931 (29), and the new RNA-seq data.

To assess performance with lower sampling frequencies, pairs of timepoints were chosen from the RNA-Seq timecourses, applied Eq. 1 to the raw $\log_2$ (TPM+1) data from those timepoints to mimic the normalization when only two timepoints are available, and then applied the predictor to those renormalized data. This was done for 102 out of the 105 timepoint pairs possible when selecting two from the 15-point timecourses; three pairings (timepoints (1, 14), (2, 15), (1, 15)) were excluded due to inadequate sample size.

Application of ZeitZeiger.

Application of ZeitZeiger (Ref. 26; herein incorporated by reference in its entirety) followed the protocol described in the ZeitZeiger package vignette (Ref. 33; herein incorporated by reference in its entirety). The same 24 timecourses used for the training were used to train ZeitZeiger, using the original $\log_2$ normalized intensity data. It was then applied to data from each of the four studies separately. In

TABLE 2

Circadian Timecourse Datasets

| | Source | Platform (GEO ID) | Total Samples | # Timecourses | Timecourse duration | Sampling frequency | # Unique subjects | Conditions per subject |
|---|---|---|---|---|---|---|---|---|
| Training/Testing | GSE39445 (27) | Custom Agilent microarray (GPL15331) | 427 | 48 | 27 h | 3 h | 26 | 2[a] |
| Validation V1 | GSE48113 (28) | Custom Agilent microarray (GPL15331) | 287 | 43 | 24 h | 4 h | 22 | 2[b] |
| Validation V2 | GSE56931 (29) | Custom Affymetrix microarray (GPL10379) | 249 | 14 | 72 h | 4 h | 14 | 3[c] |
| Validation V3 | (new) | Illumina NextSeq 500 (GPL18573) | 152 | 11 | 28 h | 2 h | 11 | 1 |

Four datasets of human blood gene expression profiling over the course of one or more circadian cycles were analyzed. The first three datasets came from published studies investigating the effect of sleep perturbations; hence, each subject in these studies has timecourse data collected under several conditions:
[a]Crossover design with two conditions/subject: "sleep extension" (control) samples follow a week of normal sleep (10 h max); "sleep restriction" samples follow a week of reduced sleep (6 h max/night).
[b]Two conditions/subject: "in-phase" (control) samples at taken at baseline; "out-of-phase" samples follow a forced desynchrony protocol to shift the sleep schedule by 12 h.
[c]Three conditions/subject: "baseline" (control) on days 1-2, "sleep deprivation" on day 3, "recovery" on day 4.

Data Preparation.

Data was expressed on a $\log_2$ scale appropriate to the platform ($\log_2$ normalized intensity for microarray data, $\log_2$ (TPM+1) for RNA-seq). Only data for genes in common to all four datasets (Table 2) were retained for analysis, resulting in a feature space of 7768 genes. For analysis by an exemplary predictor/algorithm herein, each subject's data was renormalized on a per-timecourse basis following Eq. 1.

TimeStamp Training and Feature Selection.

A random subset of 24 timecourses from the GSE39445 dataset (Ref. 27; herein incorporated by reference in its each case, the original data for the test/validation set was combined with the training data and batch-corrected with ComBat (Ref. 32; herein incorporated by reference in its entirety) via the MetaPredict (Ref. 34; herein incorporated by reference in its entirety) R package, as dictated by the ZeitZeiger protocol. ZeitZeiger was then retrained and applied to the new data.

Application of PLSR.

Application of the PLSR method (Ref. 25; herein incorporated by reference in its entirety) followed the protocol implemented in code provided by the authors (Ref. 35;

herein incorporated by reference in its entirety). Expression values were mean centered and normalized to unit variance across all 7768 genes within each sample. Leave-one-out cross-validation was used to select the optimal number of PLSR components and high-weighted genes in the training data; these values were then used to train the PLSR model using all training samples, and the resulting model was applied to the test and validation data.

Statistical Analyses.

Nonparametric Wilcoxon and Kruskal Wallis tests were used to compare distributions of errors between studies and between conditions. Empirical CDFs were computed for the error distributions, after dividing them by 12 to normalize them onto the range [0, 1]. The area under the curve was reported as the nAUC, where nAUC=0.5 for a predictor that is no better than chance and nAUC=1 for a perfect predictor. To compute statistical significance of the nAUCs, a bootstrap was used. For each study, time of day predictions were randomly generated by sampling from a uniform distribution on [0, 24) and computed the corresponding nAUC. This process was repeated 104 times to obtain a reference distribution to which the true nAUCs were compared. The true nAUCs were strongly significant with p<10-4, i.e., no simulated nAUCs exceeded those observed, indicating that both methods perform better than expected by chance.

Results

To demonstrate the accuracy of the predictors/algorithms within the scope herein, the an exemplary predictor/algorithm was applied to data from four distinct transcription profiling studies of human blood. The first three of these datasets comprise existing, publicly available microarray data from published studies (Ref. 27-29; herein incorporated by reference in their entireties). The final dataset comprises RNA-seq profiling data from eleven new subjects. Data for all four studies were restricted to the genes assayed in common across the various studies, a total of 7768 genes.

Training and Identifying Predictive Genes

A random subset comprising half of the subjects from the Möller-Levet dataset were selected to train the TimeStamp predictor. Within this training set, 10-fold cross-validation was used to tune the penalty parameters and, yielding a parsimonious model that may then be applied to other data.

Of the 7768 genes input, the model with the optimal choice of penalties comprises approximately 40 genes, achieving the desired feature selection. Because this fit is, to some degree, influenced by the random selection of training samples, this process was repeated several times to investigate the overlap of the chosen predictors. In 12 such runs, a set of 18 genes were chosen as predictors a majority of the time (Table 1). However, attempts to reduce the set of predictors to those genes alone produced greater out-of-bag and testing errors than obtained from the 40-gene models, indicating that the additional genes account for a non-negligible component of the time prediction. The variability in these "auxiliary predictors" may be due to correlated expression amongst genes. Gene timecourse expression profiles for a representative and reproducible 41-gene signature are provided as Table 1.

TABLE 1

| TimeStamp Predictive Genes | | | | | |
|---|---|---|---|---|---|
| AK5 | C12orf75 | CAMKK1 | CD1C | CD38 | CHSY1 |
| CLEC10A | CYB561 | DDIT4 | DHRS13 | DTYMK | EPHX2 |

TABLE 1-continued

| TimeStamp Predictive Genes | | | | | |
|---|---|---|---|---|---|
| FKBP4 | GHRL | GNG2 | GPCPD1 | GZMB | ID3 |
| IL13RA1 | IL1B | LLGL2 | MEGF6 | MS4A3 | MUM1 |
| NPEPL1 | NR1D1 | NR1D2 | NSUN3 | PARP2 | PDK1 |
| PER1 | PGPEP1 | POLH | REM2 | SH2D1B | SLPI |
| STIP1 | SYT11 | TCN1 | TIAM2 | ZNF438 | |

Predictive genes identified by fitting the elastic net model and applied here to infer time of day. Only 41 genes are needed for prediction. As described in the text, the predictors may vary slightly depending on the training data; repeated runs, using different training samples, consistently selected the 18 genes shown in bold.

Within-Study Accuracy

Having fit the model using the Möller Levet training subset, the predictor was applied to data from the remaining (the Test Set) to obtain time-of-day predictions for each sample based on its renormalized gene expression data. A plot comparing the predicted times to the true times for those samples is shown in the top row of the first column of FIG. 1. A plot of the proportion of samples correctly predicted as a function of the absolute time error tolerance is shown; that is, for a given value on the x-axis, the y-axis indicates the proportion of samples for which $|i|<x$ (cf Eq. 5). The lower panels of FIG. 1 depict the cumulative density of the error distribution.

It was observed that the median error was under two hours, with the vast majority (80%) of samples being predicted correctly to within slightly more than three hours. In addition, the area under the error CDF curves were computed in the lower panel. For completely random predictions, the error CDF should be a flat diagonal line, from 0% with error <0 at the lower left, to 100% with error 12 h at the upper right. To aid interpretability, the axes were normalized such that they range [0, 1], forming a unit square, and compute the area under the normalized curve (nAUC). Under the null, where predictions are no better than chance, the error CDF would have nAUC=0.5; a perfect predictor would have nAUC=1. In the Test dataset, nAUC=0.84, substantially better than chance.

Validation: Cross-Study and Cross-Platform Accuracy

The utility of a predictor depends on how well it performs when applied to data collected in other settings, where the experimental protocols, sample preparation, and possibly even the expression profiling platform may differ from the data used in training. To validate the performance of our trained predictor, the predictor was applied to data from three other independent studies: V1 (microarray data from (28)), V2 (microarray data from (29)), and V3 (new RNA-seq data).

Notably, not only were the experimental conditions (e.g., sleep protocols) different amongst the various studies (Refs. 27-29; herein incorporated by reference in their entireties), the gene expression profiling platforms also differed: V1 used the same custom Agilent microarray platform used in the training data (Ref. 28; herein incorporated by reference in its entirety), while V2 used a different Rosetta/Merck Human RSTA Custom Affymetrix 2.0 microarray (Ref. 29; herein incorporated by reference in its entirety) and the new V3 samples were profiled by RNA-Seq rather than microarray. No between-study normalization or batch correction of any sort was performed; after the standard pre-processing of each dataset, the algorithm/predictor was applied following Eqs. 1, 2, 4 5 without any additional manipulation of the data. The new data was not "recalibrated" with reference to the training data. The previously trained predictor was applied directly to each of these new datasets, without any retraining of the machine.

The results of these validation analyses are shown in the last three columns of FIG. 1. While it may be expected that systematic differences between the studies would result in diminished accuracy, the performance in the validation sets are comparable to that of the test set, with median absolute errors ranging from 1:32 to 1:53. While V1 exhibited slightly greater errors, this was not statistically significant; indeed, none of the error distributions of the validation sets differed significantly from that of the within-study Test Set (p={0.1, 1, 1} for V1, V2, V3 respectively; Wilcoxon rank-sum test) nor was there any systematic variation in error across the four datasets (p=0.1, Kruskal-Wallis). Likewise, the nAUCs obtained in those independent datasets were close to that of the Test Set, ranging from 0.80 to 0.84. The accuracy of the predictor is stable across studies and transcription profiling platforms.

Predictor Residuals Reflect Sleep Disruption

The three public datasets to which the algorithm/predictor was applied each came from studies investigating the transcriptional response to sleep-disrupting interventions: sleep restriction in the Test Set, forced desynchrony in V1, and sleep deprivation in V2. It was observed that the difference between the true and predicted time—the residuals—tends to be greater in the disrupted conditions than in the controls for each study. In the Test Set data, each participant had undergone two sleep protocols: an "extended" protocol corresponding to normal sleep, and a "restriction" protocol corresponding to a week of reduced sleep prior to the data being collected. Samples following the week of insufficient sleep are less accurately predicted than the normal sleep controls, with a median absolute error of 2:12 in the sleep-deprived group vs. 1:35 in the control group; the difference is statistically significant (p=0.006, Wilcoxon rank-sum test). In V1, participants were subject to a control and forced desychrony sleep protocol. The forced desynchrony protocol used a 28-hour day regimen, such that the subjects' sleep schedule by 4 hours each night; data was collected after three such days, when the subjects' sleep period was 12 h out of phase. It was found that the forced desychrony samples had considerably higher errors than the controls (median absolute error 2:36 vs. 1:30; 80th percentile 4:39 vs. 2:57), a difference that was highly statistically significant (p=7e-06, Wilcoxon rank-sum test). It was also found that distribution of the errors in the control group were much closer to those obtained in the Test Set; that is, the comparatively poor overall performance in the V1 dataset appears to be driven by the forced desychrony samples. The residuals for the forced desychrony samples are strongly biased (p=0.001, t-test), with the predicted times lagging the true times by ~2 h on average. These observations are indicate that the subject's internal clocks, on which predictions are based, will not align with the true time of day (leading to larger errors), and they will be systematically shifted in one direction due to the shifting sleep schedule.

A similar effect was observed in V2, a study designed to probe the effect of sleep deprivation. The data spans four days, comprising two baseline nights, a sleep-deprived night, and a recovery night. While in general the errors on all days were quite low, it was observed that most of the large deviations occurred following the sleep deprivation and during the recovery night, when the subjects' internal clocks would be the most strongly affected by the sleep deprivation.

Finally, it was noted that in the V3 data, where subjects were permitted to sleep normally (e.g., without any forced sleep deprivation or desynchrony), the error rates are quite low, similar to those of the control groups of the other datasets. Discrepancies between the predictions and the true times-of-day are physiologically driven, and are representative of underlying discrepancies between the internal and external clocks due to sleep interventions.

Prediction with Fewer Blood Draws

A key step in the application of embodiments herein is to make predictions using within-subject renormalization describe above, in which the expression level of each gene is expressed as a fold change from its mean over time in each subject (Eq. 1). All datasets used came from studies in which blood was collected every 2-4 hours over a period of one or more days, resulting in a fairly large number of samples per subject (ranging from a low of 7 in dataset V1 to a high of 18 in dataset V2). This allows computing the timecourse mean of each gene in a given subject with a low standard error, yielding more precise estimates of the fold-changes.

From a practical standpoint, however, a high sampling resolution would be unfeasibly costly and burdensome to the patient. A more realistic application would involve the minimal number of blood draws (two) at different hours of the day, ideally far enough in time that the average represents the mean over the circadian cycle. Using data from validation study V3, experiments were conducted during development of embodiments herein to investigate whether the prediction accuracy is maintained with only two samples/subject, and how the spacing of those samples affects the prediction accuracy. This was accomplished by subsetting the V3 data to two timepoints in the study (e.g., 6 am and 6 pm), recomputing the renormalized data via Eq. 1 for each subject, and applying the previously-trained predictor to the subsetted data.

Figure 2:
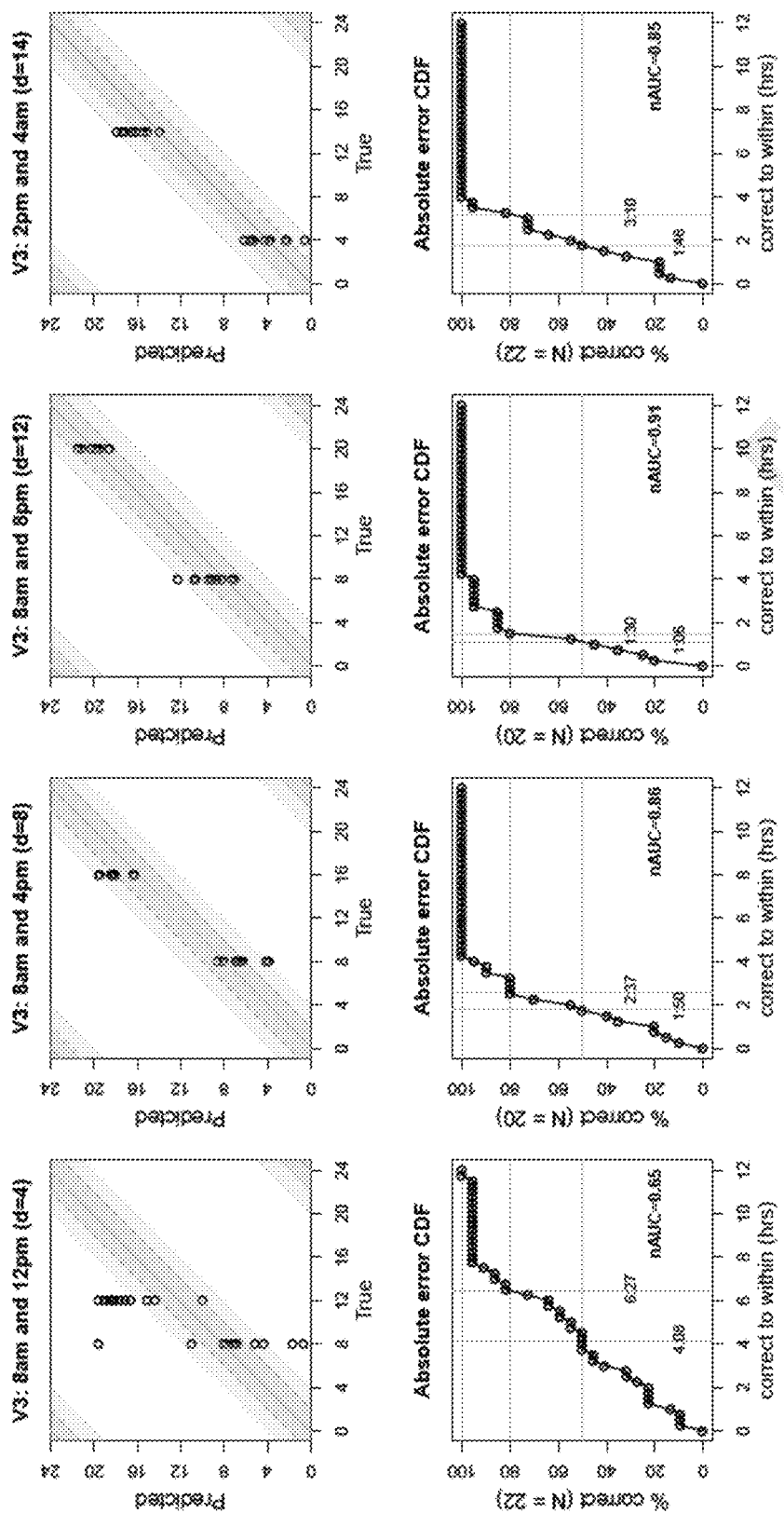
FIG. 2. Performance of exemplary methods using minimal blood draws from V3 participants. Only two timepoints per subject were used to compute the time-average gene expression required for the renormalization step (Eq. 1); the timepoints shown are spaced 4, 8, 12, and 14 hours apart. In the bottom row, the fraction of correctly predicted samples is plotted for each study vs. the size of the error. Lines indicate the median and 80th percentile errors. The N reported on the y-axes indicates the number of samples (e.g., subjects×time-points) predicted. Normalized AUCs are also given.

A plot of four examples are depicted in FIG. 2, with a selected set of timepoints 4, 8, and 12 hours apart starting at 8 am, and another set of timepoints 14 hours apart starting at 4 am. The accuracy is poorer when the timepoints are four hours apart (nAUC=0.68, with a median error of four hours), but improves considerably when the spacing widens to eight hours, at which point the median error (2 h) and nAUC (0.85) for the two timepoint case are commensurate with those obtained using the full timecourse (FIG. 1, last column). The statistics improve further with an interval of 12 hours, and then begin to slightly decrease again as the separation interval moves away from the 12 h mark. These observations are consistent with the assumption that the within-subject time average for each gene is representative of the mean expression over the course of the day; for oscillating genes with a 24 h period, the average of two antipodal samples should yield an unbiased estimate of the diurnal mean, whereas the average of closely-spaced timepoints will be biased toward the expression at a particular time of day, leading to worse predictions. It was also observed that the high accuracy appears to be independent of the specific timepoints chosen (provided that they are sufficiently far apart); the 2 pm/4 am timepoints perform as well as the 8 am/6 pm samples.

Figure 3:
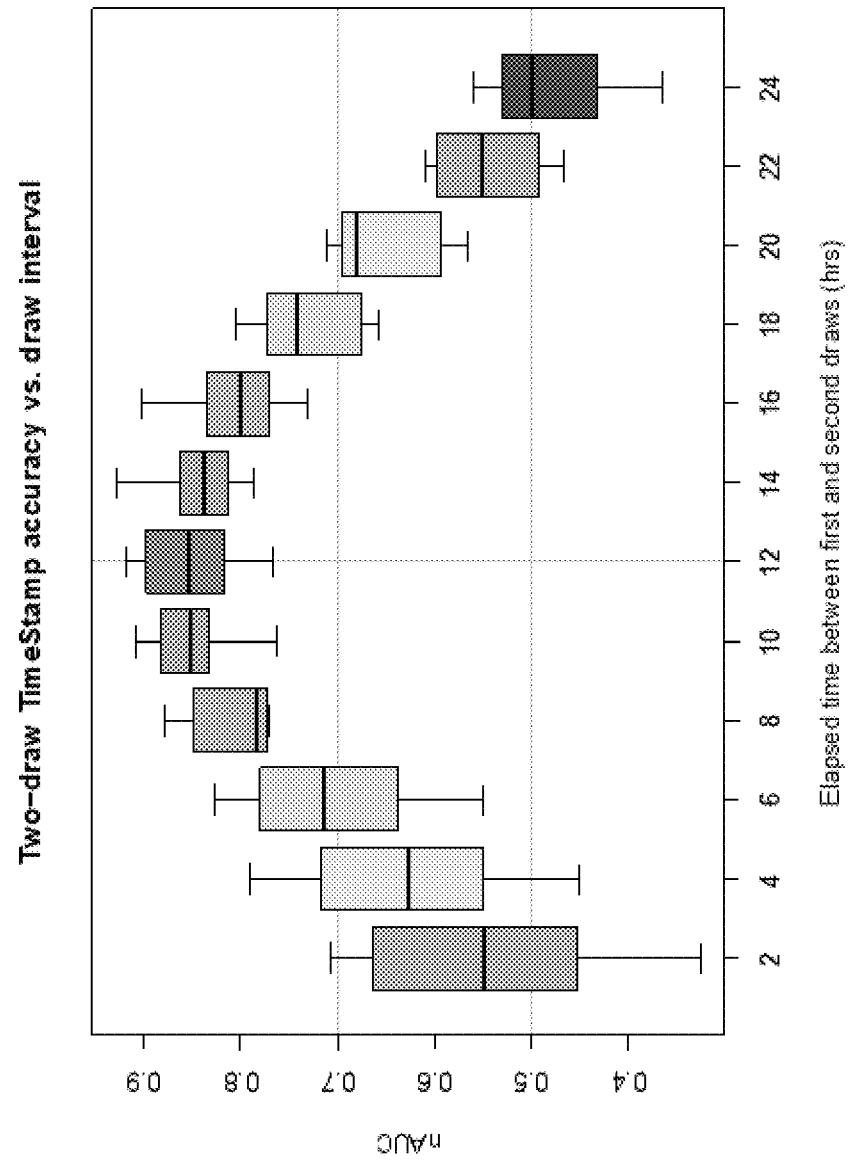
FIG. 3. Distribution of predictor accuracy in the two-draw application as a function of elapsed time between the first and second draw (V3 data). Horizontal lines are given to guide the eye at nAUC=0.5 (chance) and nAUC=0.7 (generally considered good). Boxes are colored according to the absolute time-difference modulo full days (e.g., a 20 h interval corresponds to a 4 hour difference in time-of-day). A vertical line at 12 hours indicates the axis of this symmetry.
Figure 4:
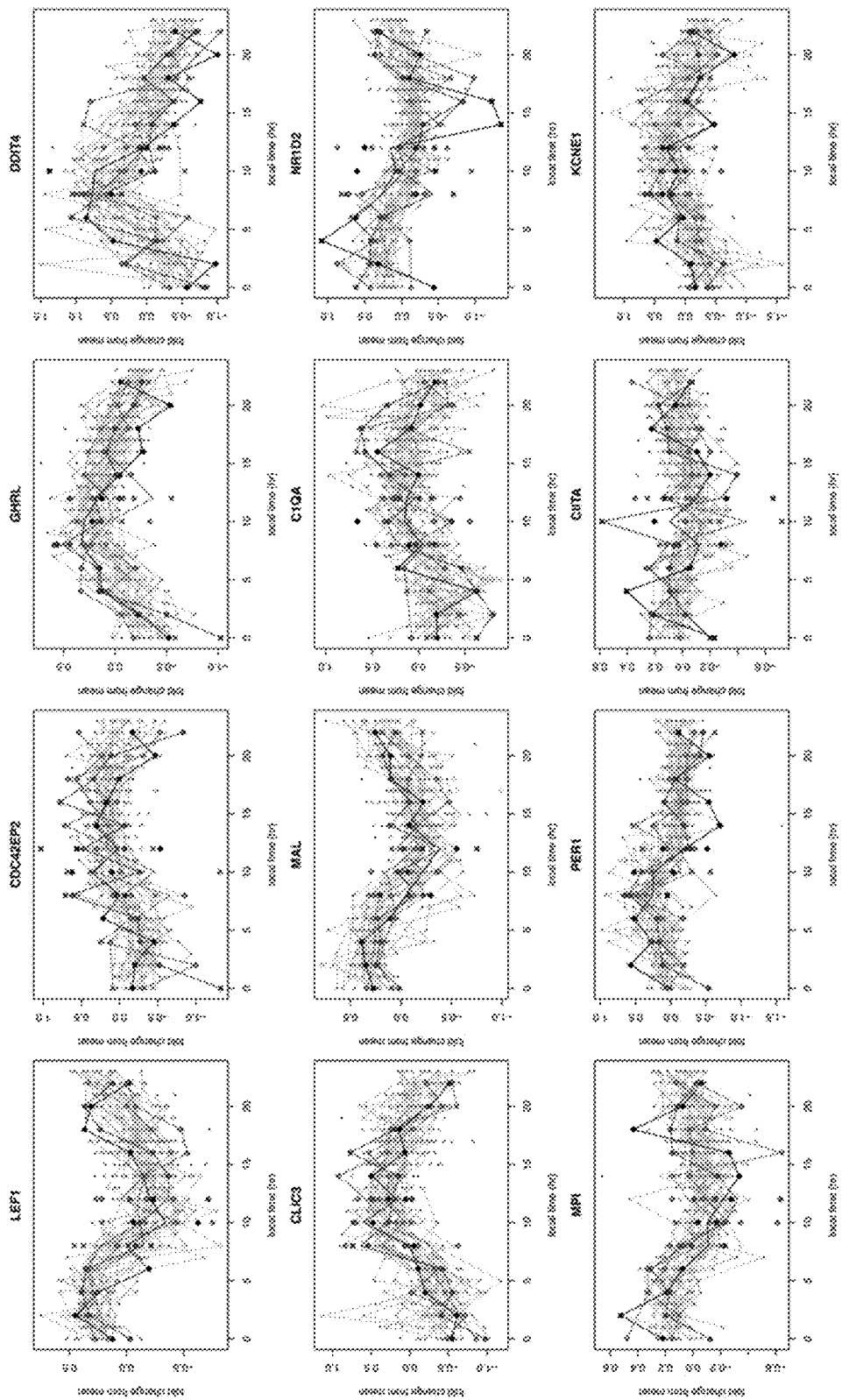
FIG. 4. Within-subject normalization: microarray data plotted with RNA-Seq data.
Figure 5:
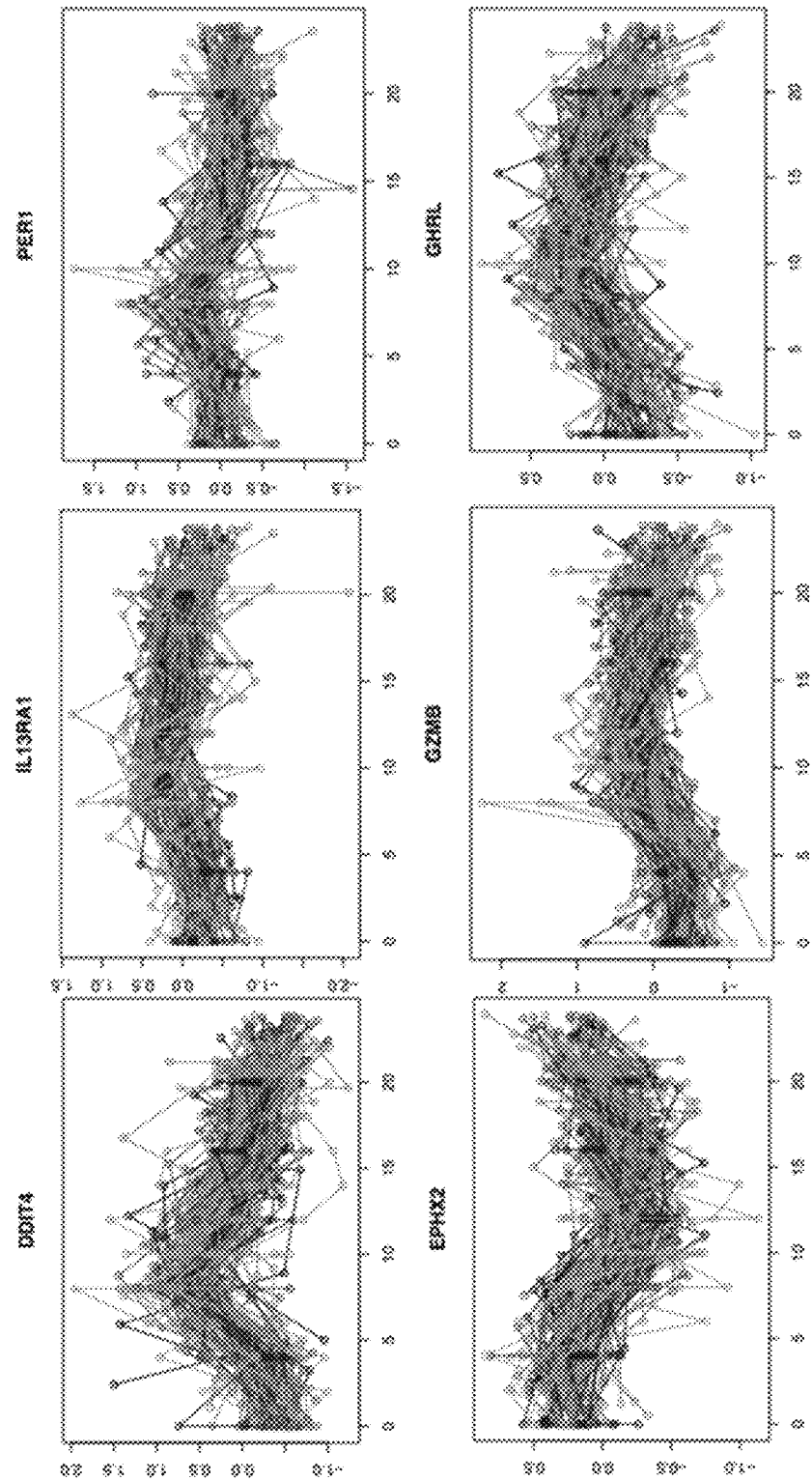
FIG. 5. Predictive genes.
Figure 6:
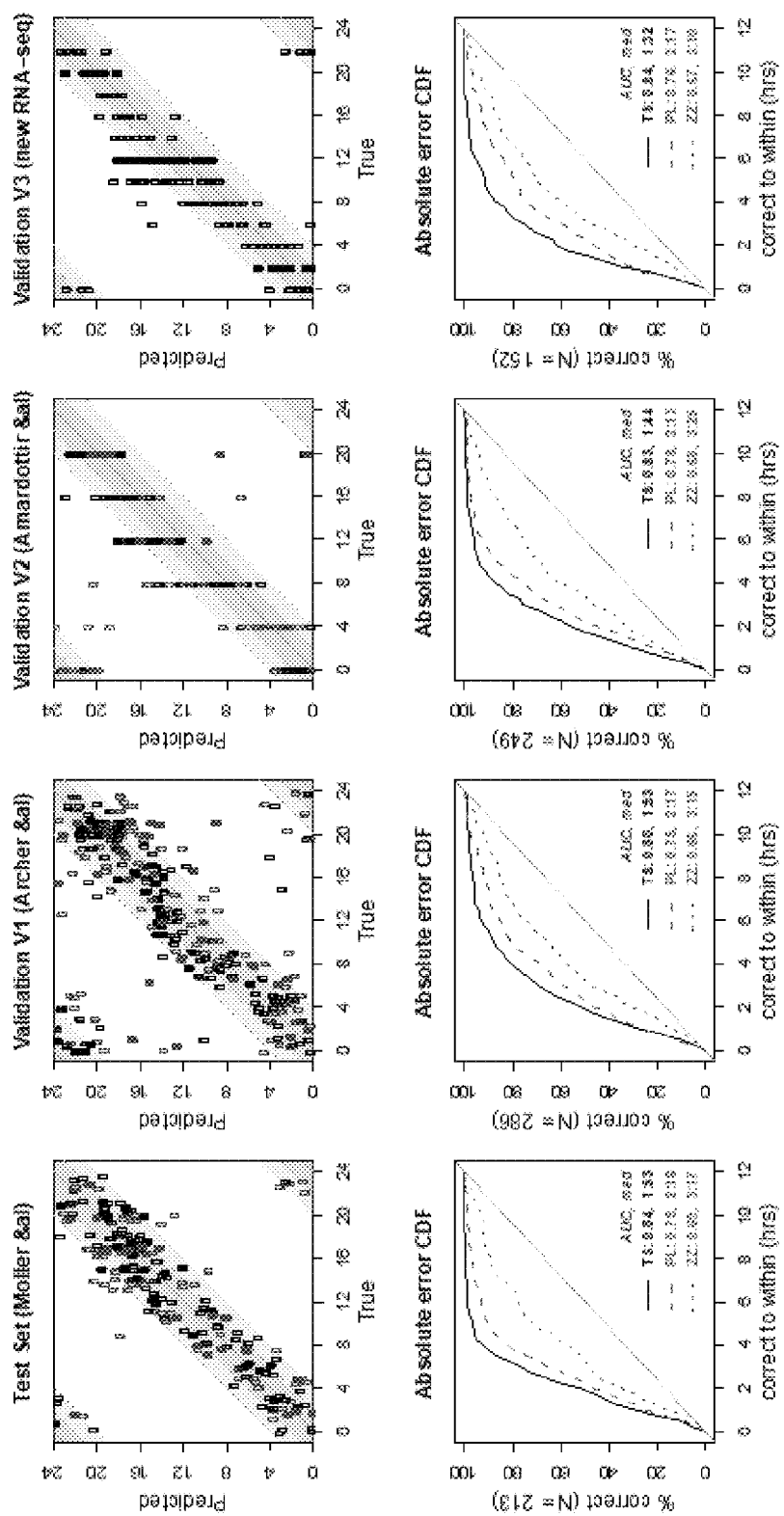
FIG. 6. Accuracy validation.
Figure 7:
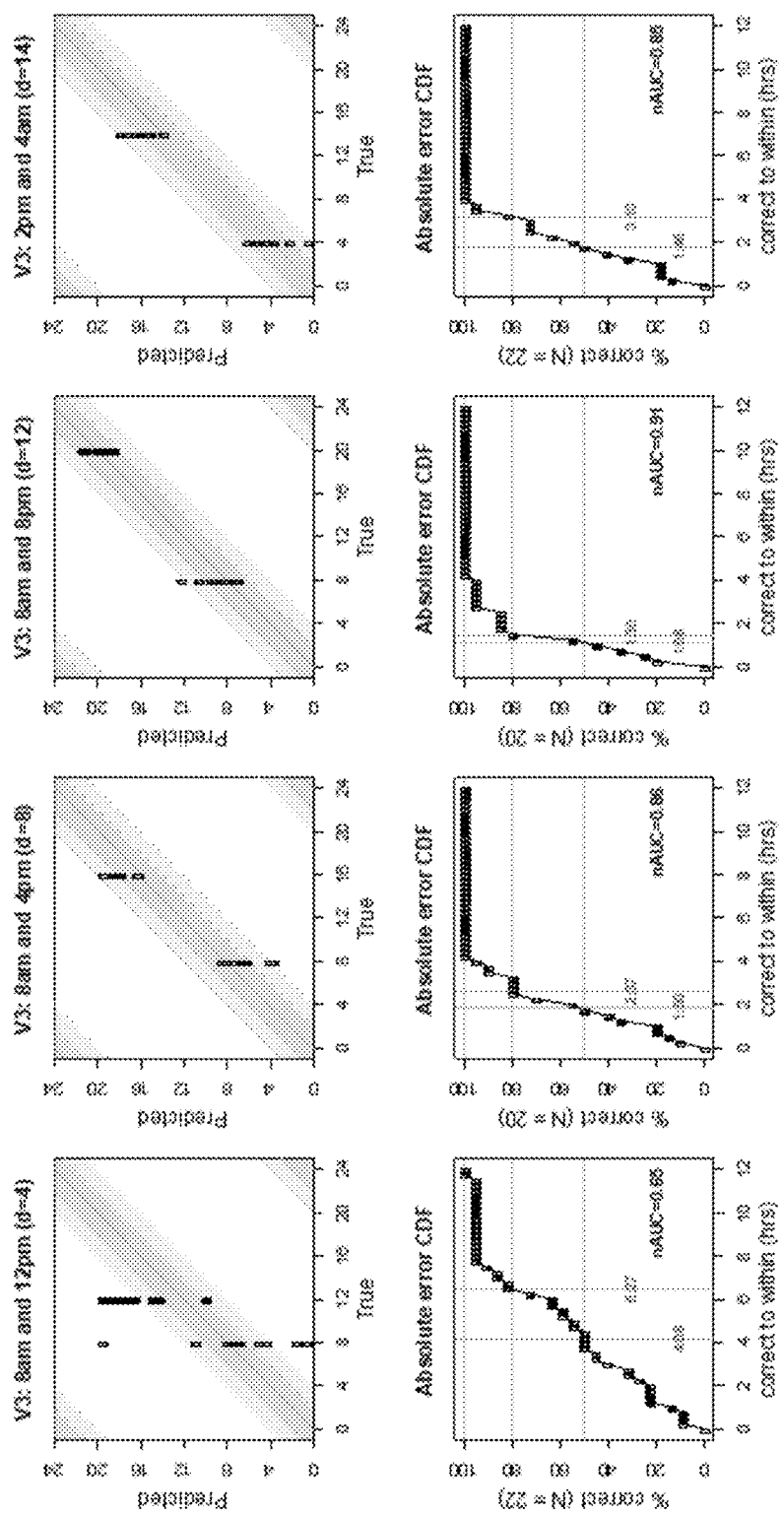
FIG. 7. Two-draw predictions.

A systematic sweep of all possible time-point pairs from the V3 study demonstrated that FIG. 2 is representative of a general pattern. FIG. 3 shows the distributions of nAUC values obtained from all the timepoint pairs separated by a given interval. (Only intervals with data for at least 3 subjects were plotted; this excluded the 26 h and 28 h intervals, which had n=2 and n=1 respectively.) A trend toward higher nAUC was observed as the interval approaches 12 h, which then decreases as the interval moves back toward 24 h, as expected. It can be seen from FIG. 3 that intervals of 10-14 h perform best, and that even intervals as narrow as 8 or 16 h yield median nAUC values >0.8. It was also observed that the distributions are narrow for those intervals, indicating that the accuracy does not depend on the beginning or ending time of the interval. It was also observed that the distributions from the 10, 12, and 14 h intervals closely overlap, indicating that a precisely antipodal samples are not required for high accuracy predictions.

Comparison to Existing Methods

Experiments were conducted during development of embodiments herein to compare the present systems/methods against other methods for inferring circadian time from gene expression (Ref. 24-26; herein incorporated by reference in their entireties). This serves as a comparison for the performance of the systems/methods herein, as well as a first attempt to apply the other methods to human validation datasets that are distinct from the training data in a manner that is representative of how they might be used in practice.

1. Molecular Timetable.

Ueda and colleagues originally proposed a "Molecular Timetable" method for assessing circadian time in the mouse liver using a complement of 50 rhythmic genes that exhibited unique peak times (Ref. 23; herein incorporated by reference in its entirety). By assessing the transcript levels of these "time-indicating genes" at a single time of day, they found that they could accurately (±1.5 h SD) determine the time of day that the liver was taken from the mouse based on the relative expression levels of the time-indicating genes. Performance in human data was not evaluated in the original publication as the method predated human circadian datasets; however, subsequent application to human data (Ref. 24, 25; herein incorporated by reference in their entireties) indicated that it is strongly outperformed by more recent methods. Accordingly, further comparisons to Molecular Timetable were not pursued.

2. ZeitZeiger.

Hughey and coworkers proposed "ZeitZeiger," a supervised machine learning method to predict time of day from high-dimensional observations (Ref. 26; herein incorporated by reference in its entirety). This method models each feature as a periodic spline with constant variance, generates a new set of observations by discretizing the spline fit, applies sparse principal component (SPC) projection of the new features to obtain a reduced set of predictors, and then uses a maximum likelihood estimator to predict the time of day. Parameters for the algorithm (including the number of spline knots, the number of discretization points, the penalty for the SPC regularization, and the number of SPC components) are chosen based on heuristics or tuned using cross-validation.

The authors originally applied ZeitZeiger to data from a large set of transcription profiling studies comprising a variety of mouse tissues, demonstrating much higher accuracy using a smaller number of genes than was obtained using the Molecular Timetable approach. A follow-up work applied ZeitZeiger to human data from three published studies (Ref. 24; herein incorporated by reference in its entirety). Data from the three studies were first combined, renormalized with respect to one-another, and then batch-corrected using ComBat (Ref. 32; herein incorporated by reference in its entirety) to remove any systematic differences in the study platforms; this yielded a combined dataset of 498 samples from 60 unique individuals. ZeitZeiger's performance was then assessed using subject-wise cross-validation (e.g., keeping all samples from the same subject in the same fold), yielding a median absolute error of 2.1 h for the best choice of parameter values amongst the cross-validation sets.

In contrast to ZeitZeiger, the methods/systems herein do not impose a periodic model upon the predictors. More importantly, the methods/systems herein do not necessitate that data from different studies be batch corrected, as ZeitZeiger does, avoiding several drawbacks associated with this approach. In particular, application of ZeitZeiger to new data (such as that of a new patient) requires re-normalizing and batch correcting the new data with the training data and then retraining the machine. This process is both computationally intensive and results in a different predictive model every time ZeitZeiger is applied to new data, meaning that the model that predicts time from gene expression is not universal or comparable between runs. As a result, it would be difficult to compare results for a patient over time to monitor disease progression or treatment response. Moreover, the use of cross-validation can underestimate the error in the multi-batch case, since some subjects from each batch will be included in the training data for every CV fold; no assessment was made (Ref. 24; herein incorporated by reference in its entirety) of how it might perform in a validation dataset comprising a distinct batch that does not contribute in any way to the training data.

3. PLSR and Differential PLSR.

A method based on partial least squares regression (PLSR) was also recently proposed for application in human data (Ref. 25; herein incorporated by reference in its entirety). Like ZeitZeiger, the PLSR-based method also takes a machine-learning approach to generate a parsimonious predictor from the full set of gene expression measurements. Unlike ZeitZeiger, however, the PLSR-based method does not impose a periodic spline model on the genes, and thus has fewer parameters that need to be set by the user (two parameters, the number of PLS components and the number of genes used in the model, are selected by cross-validation). The authors also considered a "differential PLSR" method, in which the differences in gene expression values from two draws 12 h apart were used as the predictors, rather than the gene expression values themselves.

To demonstrate the performance of the PLSR approach, the authors applied it to the combined data from two published studies. Because these two datasets used the same microarray platform, little re-normalization and no batch-correction was needed. The combined data was then split into training and testing subsets comprising 329 and 349 samples, respectively, with balanced amounts of data from each study in the training and testing sets. Parameters were tuned using cross-validation in the training set, and accuracy was assessed in the held-out testing samples. Performance using the same training/testing subsets were then compared with that of the Molecular Timetable (which had not been previously applied to human data) and ZeitZeiger (which had only previously reported "out of bag" errors from the cross-validation, but not assessed the tuned predictors performance in a separate testing or validation dataset). The PLSR-based method exhibited a median absolute error of 1.9 h compared to 2.8 h for ZeitZeiger and 2.6 h for the Molecular Timetable. Using the differential PLSR approach, the authors were able to improve performance to a median absolute error of 1.1 h using a PLSR model using set of 100 genes.

However, the performance of this approach in a distinct validation dataset remained unclear. While PLSR avoided the issues associated with batch correction, the fact that the studies being combined used identical microarray platforms eliminated considerable technical variability. Confining the method to use a specific microarray platform greatly limits the practical utility of the predictor, especially with rapidly evolving high-throughput technologies; on the other hand, performance with other platforms is unknown. Moreover, because the predictor was trained on a balanced mixture of the two datasets, it is not possible to tell how it would perform in a truly separate dataset. As in ZeitZeiger, training and testing on mixtures of datasets makes it impossible to assess the method's sensitivity to systematic technical variations that are likely to occur when the method is used in practice (e.g., differences between platforms, sample handling, and laboratory protocols).

Even though the final PLSR predictor uses a selected set of 100 genes, an initial algorithmic step of z-scoring each sample across all genes requires assaying all ~26,000 genes on the original array in order to obtain the z-scores for the predictive markers. As a result, any application of the predictor also requires assaying 26,000 genes (the vast majority of which will not be used) in order to properly calibrate the z-scores for the 100 predictors. This cumbersome requirement may also limit the method's translatability to practical application. In contrast, the predictors/algorithms herein are readily applied simply by assaying, for example, the 41 identified markers.

Predictor/Algorithm Herein Outperforms ZeitZeiger and PLSR in Multiple Independent Datasets To compare performance of the systems/methods herein to exiting methods and to assess their generalizability and cross-platform accuracy, a head-to-head comparison was performed. To ensure consistency all methods were trained using the same samples that had been used to train in other experiments herein, and applied to the same testing and validation samples (Table 2).

For ZeitZeiger, R packages provided by the author were used. Following ZeitZeiger's published instructions, combined and batch-corrected the pre-processed gene expression data from all four studies (Table 2) using the MetaPredict library. Then the ZeitZeiger method was applied using the published code (Ref. 33; herein incorporated by reference in its entirety). Herein is reported the accuracy in the testing and validation sets using a ZeitZeiger predictor that had been trained on the Möller-Levet training subset.

For the PLSR-based approach, the authors' protocol and published code was used (Refs. 25, 35; herein incorporated by reference in their entireties)) The initial z-scoring step was applied across all genes; in the case, the 7768 genes in common across all four datasets. Using the same subset of the Möller-Levet data used to train TimeStamp and ZeitZeiger, leave-one-out cross-validation was performed to select the optimal number of PLSR components (5) and genes with the highest weights (100) were re-fitted the PLSR model against the complete training data as the final predictor. The trained model was then applied to the remaining 900 samples from the four studies, enabling direct comparison of TimeStamp, Zeitzeiger, and PLSR.

The bottom row of panels in FIG. 1 illustrates the accuracy obtained in human data using ZeitZeiger and PLSR compared with the systems and methods herein. For ZeitZeiger, median absolute errors exceeded 3 h in all datasets, with nAUCs ranging from 0.65 to 0.68; while these were better than random chance, they were significantly lower than the nAUCs obtained with TimeStamp. Consistent with prior findings (25), PLSR outperforms ZeitZeiger, with median absolute errors of ~2.25 h and nAUCs between 0.75 and 0.79. Methods herein consistently and significantly outperform PLSR in all validation datasets with median absolute errors under 2 h and nAUCs exceeding 0.80. Moreover, this accuracy is achieved using fewer predictors (41 genes versus 100 for PLSR).

No significant relationship was found between magnitude of the ZeitZeiger or PLSR errors and the sleep disrupting interventions in the Test, V1, and V2 datasets. The error distributions of the sleep deprivation/forced desynchrony samples did not significantly differ from those of the control subjects in any experiment (all p ≥0.1, Wilcoxon rank sum tests).

REFERENCES

The following references, some of which are cited above by number, and herein incorporated by reference in their entireties.

1. Ko C H, Takahashi J S (2006) Molecular components of the mammalian circadian clock. Hum Mol Genet 15 Spec No 2:R271-7.
2. Boivin D B, et al. (2003) Circadian clock genes oscillate in human peripheral blood mononuclear cells. Blood 102(12):4143-5.
3. Zhang R, Lahens N F, Ballance H I, Hughes M E, Hogenesch J B (2014) A circadian gene expression atlas in mammals: implications for biology and medicine. Proceedings of the National Academy of Sciences 111(45):16219-16224.
4. Eastman C, Gazda C, Burgess H, Crowley S, Fogg L (2005) Advancing circadian rhythms before eastward flight: a strategy to prevent or reduce jet lag. Sleep 28(1):33-44.
5. Barion A, Zee P C (2007) A clinical approach to circadian rhythm sleep disorders. Sleep Med 8(6):566-77.
6. Shields M (2002) Shift work and health. Health Reports 13(4):11-33.
7. Roenneberg T, et al. (2007) Epidemiology of the human circadian clock. Sleep Med Rev 11(6):429-38.
8. Puttonen S, Harma M, Hublin C (2010) Shift work and cardiovascular disease—pathways from circadian stress to morbidity. Scand J Work Environ Health 36(2):96-108.
9. Lemmer B (2006) Clinical chronopharmacology of the cardiovascular system: hypertension and coronary heart disease. Clin Ter 157(1):41-52.
10. Roenneberg T, Wirz-Justice A, Merrow M (2003) Life between clocks: daily temporal patterns of human chronotypes. J Biol Rhythms 18(1):80-90.
11. Jones C R, et al. (1999) Familial advanced sleep-phase syndrome: A short-period circadian rhythm variant in humans. Nat Med 5(9):1062-5.
12. Chang A M, Reid K J, Gourineni R, Zee P C (2009) Sleep timing and circadian phase in delayed sleep phase syndrome. J Biol Rhythms 24(4):313-21.
13. Toh K L, et al. (2001) An hper2 phosphorylation site mutation in familial advanced sleep phase syndrome. Science 291(5506):1040-3.
14. Xu Y, et al. (2005) Functional consequences of a CKIdelta mutation causing familial advanced sleep phase syndrome. Nature 434(7033):640-4.
15. Doherty C J, Kay S A (2010) Circadian control of global gene expression patterns. Annu Rev Genet 44:419-44.
16. Levi F, Schibler U (2007) Circadian rhythms: mechanisms and therapeutic implications. Annu Rev Pharmacol Toxicol 47:593-628.
17. Videnovic A, et al. (2014) Circadian melatonin rhythm and excessive daytime sleepiness in parkinson disease. JAMA Neurol 71(4):463-9.

18. Benloucif S, et al. (2005) Stability of melatonin and temperature as circadian phase markers and their relation to sleep times in humans. J Biol Rhythms 20(2):178-88.
19. Stratmann M, Schibler U (2006) Properties, entrainment, and physiological functions of mammalian peripheral oscillators. J Biol Rhythms 21(6):494-506.
20. Archer S N, Viola A U, Kyriakopoulou V, von Schantz M, Dijk D J (2008) Inter-individual differences in habitual sleep timing and entrained phase of endogenous circadian rhythms of BMAL1, PER2 and PER3 mRNA in human leukocytes. Sleep 31(5):608-17.
21. Patel V R, Eckel-Mahan K, Sassone-Corsi P, Baldi P (2012) CircadiOmics: integrating circadian genomics, transcriptomics, proteomics and metabolomics. Nature methods 9(8):772-773.
22. Patel V R, et al. (2015) The pervasiveness and plasticity of circadian oscillations: the coupled circadian-oscillators framework. Bioinformatics p. btv353.
23. Ueda H R, et al. (2004) Molecular-timetable methods for detection of body time and rhythm disorders from single-time-point genome-wide expression profiles. Proc Natl Acad Sci USA 101(31):11227-32.
24. Hughey J J (2017) Machine learning identifies a compact gene set for monitoring the circadian clock in human blood. Genome Medicine 9(1):19.
25. Laing E E, et al. (2017) Blood transcriptome based biomarkers for human circadian phase. eLife 6:e20214.
26. Hughey J J, Hastie T, Butte A J (2016) ZeitZeiger: supervised learning for high-dimensional data from an oscillatory system. Nucleic acids research 44(8):e80-e80.
27. Moller-Levet C S, et al. (2013) Effects of insufficient sleep on circadian rhythmicity and expression amplitude of the human blood transcriptome. Proc Natl Acad Sci USA 110(12):E1132-41.
28. Archer S N, et al. (2014) Mistimed sleep disrupts circadian regulation of the human transcriptome. Proceedings of the National Academy of Sciences 111(6):E682-E691.
29. Arnardottir E S, et al. (2014) Blood-gene expression reveals reduced circadian rhythmicity in individuals resistant to sleep deprivation. Sleep 37(10):1589.
30. Zou H, Hastie T (2005) Regularization and variable selection via the elastic net. Journal of the Royal Statistical Society Series B-Statistical Methodology 67:301-320.
31. Friedman J, Hastie T, Tibshirani R (2010) A note on the group lasso and a sparse group lasso. arXiv preprint arXiv:1001.0736.
32. Johnson W E, Li C, Rabinovic A (2007) Adjusting batch effects in microarray expression data using empirical bayes methods. Biostatistics 8(1):118-127.
33. Hughey J J (2016) ZeitZeiger package vignette (github.com/jakejh/zeitzeiger), v.0.0.0.9021 edition.
34. Hughey J J (2016) MetaPredict package vignette (github.com/jakejh/metapredict), v.0.0.0.9005 edition.
35. Laing E E, et al. (2017) Source code and data for "blood transcriptome based biomarkers for human circadian phase". sleep-sysbio.fhms.surrey.ac.uk/PLSR_16/p. Downloaded: 8 Mar. 2017.
36. Wheeler D, et al. (2007) Database resources of the National Center for Biotechnology Information. Nucleic acids research 35(Database issue):D5.
37. Davis S, Meltzer P (2007) GEOquery: a bridge between the Gene Expression Omnibus (GEO) and BioConductor. Bioinformatics 14:1846-1847.
38. R Core Team (2015) R: A Language and Environment for Statistical Computing (R Foundation for Statistical Computing, Vienna, Austria).

The invention claimed is:

1. A method of determining the biological time-of-day of a subject, the method comprising:
    (a) detecting the level of one or more biomarkers in two or more samples obtained at different timepoints from the subject, wherein at least two of the timepoints are spaced by at least 4 hours, wherein the biomarkers are selected from c-type lectin domain containing 10a (CLEC10A), ghrelin and obestatin prepropeptide (GHRL), CD1C molecule (CD1C), dehydrogenase/reductase 13 (DHRS13), t-lymphoma invasion and metastasis-inducing protein 2 (TIAM2), granzyme B (GZMB), epoxide hydrolase 2 (EPHX2), and pyruvate dehydrogenase kinase 1 (PDK1);
    (b) applying a predictor algorithm to the levels of biomarkers detected in the two or more samples; and
    (c) determining the biological time-of-day for the subject based on output of the predictor algorithm.

2. The method of claim 1, wherein the samples are a blood sample.

3. The method of claim 1, wherein the level of 10 or more biomarkers selected from AK5, CLEC10A, FKBP4, IL3RA1, NPEPL1, PER1, STIP1, C12orf75, CYB561, GHRL, IL1B, NR1D1, PGPEP1, SYT11, CAMKK1, DDIT4, GNG2, LLGL2, NR1D2, POLH, TCN1, CD1C, DHRS13, GPCPD1, MEGF6, NSUN3, REM2, TIAM2, CD38, DTYMK, GZMB, MS4A3, PARP2, SH2D1B, ZNF438, CHSY1, EPHX2, ID3, MUM1, PDK1, and SLPI are detected.

4. The method of claim 1, wherein the level of one or more of CLEC10A, PER1, GHRL, IL1B, NR1D1, DDIT4, GNG2, LLGL2, NR1D2, CD1C, DHRS13, GPCPD1, TIAM2, CD38, GZMB, ZNF438, EPHX2, and PDK1 are detected.

5. The method of claim 4, wherein the level of each of CLEC10A, PER1, GHRL, IL1B, NR1D1, DDIT4, GNG2, LLGL2, NR1D2, CD1C, DHRS13, GPCPD1, TIAM2, CD38, GZMB, ZNF438, EPHX2, and PDK1 are detected.

6. The method of claim 5, wherein the level of each of the biomarkers selected from AK5, CLEC10A, FKBP4, IL3RA1, NPEPL1, PER1, STIP1, C12orf75, CYB561, GHRL, IL1B, NR1D1, PGPEP1, SYT11, CAMKK1, DDIT4, GNG2, LLGL2, NR1D2, POLH, TCN1, CD1C, DHRS13, GPCPD1, MEGF6, NSUN3, REM2, TIAM2, CD38, DTYMK, GZMB, MS4A3, PARP2, SH2D1B, ZNF438, CHSY1, EPHX2, ID3, MUM1, PDK1, and SLPI are detected.

7. The method of claim 1, wherein the biomarker levels are detected by microarray or RNA-Seq.

8. The method of claim 1, wherein the predictor algorithm comprises a within-subject normalization procedure.

9. The method of claim 1, wherein detecting the level of one or more biomarkers comprises detecting the level of gene expression of the one or more biomarkers.

* * * * *

UNITED STATES PATENT AND TRADEMARK OFFICE
CERTIFICATE OF CORRECTION

| | |
|---|---|
| PATENT NO. | : 11,328,790 B2 |
| APPLICATION NO. | : 16/000607 |
| DATED | : May 10, 2022 |
| INVENTOR(S) | : Rosemary Braun, Ravi Allada and Phyllis Zee |

It is certified that error appears in the above-identified patent and that said Letters Patent is hereby corrected as shown below:

On the Title Page

(72) Inventors should read:
Rosemary Braun, Chicago, IL (US);
Ravi Allada, Glenview, IL (US);
Phyllis Zee, Chicago, IL (US)

Signed and Sealed this
Fourth Day of October, 2022

Katherine Kelly Vidal
*Director of the United States Patent and Trademark Office*